(12) United States Patent
Sinha et al.

(10) Patent No.: US 6,969,778 B2
(45) Date of Patent: Nov. 29, 2005

(54) **DDQ MEDIATED ONE STEP DIMERIZATION OF β-ASARONE OR β-ASARONE RICH *ACORUS CALAMUS* OIL IN THE FORMATION OF NOVEL NEOLIGNAN**

(75) Inventors: Arun Kumar Sinha, Himachal Pradesh (IN); Bhupendra Prasad Joshi, Himachal Pradesh (IN); Ruchi Acharya, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/660,556

(22) Filed: Sep. 12, 2003

(65) Prior Publication Data

US 2004/0049085 A1 Mar. 11, 2004

Related U.S. Application Data

(62) Division of application No. 10/108,269, filed on Mar. 28, 2002, now abandoned.

(51) Int. Cl.$^7$ ............................................. C07C 41/18
(52) U.S. Cl. ........................ 568/646; 568/322; 568/648
(58) Field of Search ................................ 568/646, 322, 568/648, 644, 312, 315, 316, 318, 323, 324

(56) References Cited

U.S. PATENT DOCUMENTS

| | | | |
|---|---|---|---|
| 3,769,350 | A | 10/1973 | Perry et al. |
| 4,540,709 | A | 9/1985 | Chang et al. |
| 4,873,349 | A | 10/1989 | Robin et al. |
| 5,639,782 | A | 6/1997 | Shen et al. |
| 6,136,992 | A | 10/2000 | Ram et al. |
| 6,590,127 | B1 * | 7/2003 | Sinha et al. ................. 568/315 |

OTHER PUBLICATIONS

Bohlmann et al., The active substances of Asarum europeum L. XV. Structure of the diasarones, May 1982, vol. 315(5), pp. 474–476.*
Kawazoe, et al.; *J. Nat. Prod.*; 2001; vol. 64; 588–591.
Motley; Economic Botany; 1994; vol. 48; 397–412.
Stauffer, et al.; *J. Med. Chem.* 2000; vol. 43; 4934–4947.
Meyers, et al., *J. Med. Chem.*; 2001; vol. 44, 4230–3251.
Rao and Rao; *Journal of Natural Products*; Jan. 1990; vol. 53; No. 1; 212–215.
Suri, et al.; *Indian Journal of Chemistry*; Jun. 1987; vol. 26B; 587–588.
Poplawski, et al.; *J. Med. Chem.*; 2000; vol. 43; 3671–3676.
Högberg, et al.; *J. Med. Chem.*; 1990; vol. 33; 1155–1163.
Parmar, et al.; *Phytochemistry*; 1997; vol. 46; No. 4; 597–627.
Mohagheghzadeh, et al.; *J. Nat. Prod.*: 2002; vol. 65; 69–71.
Charlton; *J. Nat. Prod.*; 1998; vol. 61; 1447–1451.
Hu, et al.; *Planta Med.*; 2000; vol. 66; 662–664.
Keller, et al.; *Planta Medica*; 1985; 6–9 (Abstract in English).
Nigam, et al.; *Indian Perfumer*; 1990; vol. 34; No. 4; 282–285.
Choudary, et al.; *Indian Journal of Chemistry*; Mar. 1997; vol. 36B; 278–280.
Dung, et al.; *J. Essent. Oil Res.*; Jan. 2, 1995; vol. 7; 111–112.
Abel; *Planta Medica*; 1987; 251–253 (Abstract in English).
Hemandez, et al.; *Planta Med.*; 1993; vol. 49; 121–124.
Filleur, et al.; *Planta Med.*; 2001; vol. 67; 700–703.
Lopez; *Plant Med.*; 1993; vol. 59; 115–119.
Nagase, et al.; *Planta Med.*; 2001; vol. 67; 705–708.
Ikarashi, et al.; *Planta Med.*; 2001; vol. 67; 709–713.
Shimomura, et al.; *Phytochemistry*; 1987; vol. 26; No. 5; 1513–1515.
Clark–Lewis and V. Nair; *Flavan Derivatives*; vol. XVI; 2141–2149.
Kumar; *J. Org. Chem.*; 1985; vol. 50; 3070–3073.
Doering and Berson; *J.A.C.S.*; 1950; vol. 72; 1118–1123.
Lazutka, et al.; *Food and Chemical Toxicology*; 2001; vol. 29; 485–492.
Oprean, et al.; *Journal of Pharmaceutical and Biomedical Analysis*; 1998; vol. 18; 227–234.
Oprean, et al.; *Journal of Pharmaceutical and Biomedical Analysis*; 2001; vol. 24; 1163–1168.
Oprean, et al.; *Journal of Pharmaceutical and Biomedical Analysis*; 1998; vol. 18, 651–657.
Garduño, et al.; *Journal of Ethnopharmacology*; 1997; vol. 55; 161–163.
Jaimol, et al.; *Applied Catalysis A: General*; 2001; vol. 214; 1–10.
Juhász, et al.; *J. Nat. Prod.*; 2000; vol. 63; 866–870.
Ahn, et al.; *J. Nat. Prod.*; 2001; vol. 64; 1562–1564.
Kikuzaki, et al.; *Phytochemistry*; 2001; vol. 56; 109–114.
Enqiquez, et al., *Phytochemistry*; 1980; vol. 19; 2024–2025.
Hampl, et al.; *Casopis Lakaru Ceskych*; 2000; vol. 139; Supp. 1; 31–33 (Abstract).
Huynh, et al.; *Archives of Biochemistry and Biophysics*; Oct. 1986; vol. 250; Iss. 1; 186–196 (Abstract).
Juhasz, et al.; *Journal of Natural Products*; 2000; vol. 62; Iss. 6; 866–860 (Abstract).
Curró, et al.; *Journal of Chromatography A*; 1987; vol. 404; 273–278 (Abstract).

(Continued)

*Primary Examiner*—Rosalynd Keys
(74) *Attorney, Agent, or Firm*—Foley & Lardner LLP

(57) ABSTRACT

The present invention relates to neolignan (NEOLASA-I) 3-ethyl-2-methyl-3-(2",4",5"-trimethoxy-phenyl-1-(2',4',5'-trimethoxy)phenyl-1-propene and a process for the preparation of high purity, higher yield neolignan, α-asarone, 2,4,5-trimethoxy-phenyl propionone from β-asarone or β-asarone rich *Acorus calamus* oil containing α and γ-asarone by hydrogenating and dimerizing by treatment with DDQ in presence of an organic acid.

7 Claims, 9 Drawing Sheets

OTHER PUBLICATIONS

Mazza; *Journal of Chromatography A*; 1985; vol. 328; 179–194 (Abstract).
Hwu, et al., *J. Med. Chem.*; 1998; vol. 41; No. 16; 2994–3000.
Chen, et al.; *J. Med. Chem.*; 1998; vol. 41; No. 16; 3001–3007.
Donnelly, et al.; *Tetrahedron Letters*; 1991; vol. 32; No. 31; 3835–3836.
Juhász, et al.; *Tetrahedron Letters*; 2000; vol. 41; 2491–2494.
Minato, et al.; *Tetrahedron Letters*; 1980; vol. 21; 4017–4020.
Becker and Beroza; *Tetrahedron Letters No. 4*; 1962; 157–163.
Yamamura, et al.; *Tetrahedron Letters*; 1978; vol. 49; 4981–4894.
Gezginci and Timmermann; *Tetrahedron Letters*; 2001; vol. 42; 6083–6085.
Kadota, et al.; *Tetrahedron Letter*; 1987; vol. 28; No. 25; 2857–2860.
Dhal, et al.; *Tetrahedron*; 1994; vol. 50; No. 4; 1153–1164.
Syrjänen and Brunow; *Tetrahedron*; 2001; vol. 57;365–370.
Robin and Landais; *Tetrahedron*; 1992; vol. 48; No. 5; 819–830.
MacMillan, et al.; *Tetrahedron*; 1969; vol. 25; 905–914.
Ward; *Tetrahedron*; 1990; vol. 46; No. 15; 5029–5041.
Chattopadhyay and Rao; *Tetrahedron*; 1987; vol. 43; No. 4; 669–678.
Schiestl, et al.; *Mutation Research*; 1989; vol. 224; Iss. 4; 427–436 (Abstract)
Kim, et al.; *Carcinogenesis*; 1999; vol. 20; Iss. 7; 1303–1307 (Abstract).
Kikuchi, et al.; *Chem. Pharm. Bull.*; 1983; vol. 31; No. 3; 1112–1114.
Perry, et al.; *J. Org. Chem.*; 1972; vol. 37; No. 26; 4371–4376.
Tanaka, et al.; *Bioorganic & Medicinal Chemistry Letters 12*; 2002; 623–627.
Jensen, et al.; *Phytochemistry*; 1993; vol. 33; No. 3; 523–530.
Dias; *Phytochemistry*; 1988; vol. 27; No. 9; 3008–3009.
Badheka, et al.; *Phytochemistry*; 1987; vol. 26; No. 7; 2033–2036.
Saxena; *Phytochemistry*; 1986; vol. 25; No. 2; 553–555.
Wenkert, et al.; *Phytochemistry*; 1976; vol. 15; 1547–1551.
Moss; *Pure Appl. Chem.*; 2000; vol. 72; No. 8; 1493–1523.
MacRae and Towers; *Phytochemistry*; 1984; vol. 23; No. 6; 1207–1220.
Sachio, et al.; Abstract of EP0597107 A4; 1994.
Masaaki, et al.; Abstract of JP2001139579; 2001.
Liu et al., "Chemical Structure of 1,3-bis (2,4, 5-trimethoxy)phynyl-2-pentene-1," *Fenxi Hauxue*, 1994, vol. 22, No. 4, pp. 355–358.
Lander et al. "Light–Induced Transformation of Ararone," *Flavour and Fragance Journal*, 1991, vol. 6, No. 1, pp. 21–28.
Lemini et al., "Structure of (E)–1–myhtyl–1,3–bis(2,4, 5–thimethoxyphenyl)–1–pentene and 1(2,4, 5–thimethoxyphenyl)–2–methyl–3–ethyl–. . . Asarone Dimers," *Acta Crystallographica*, Section C: Crystal Structure Communications, 1990, vol. C46, No. 8, pp. 1542–1545.

Bohlmann et al., "The Active Substances of Asarum Europeum L. XV Structure of the Diasarones," *Archiv der Pharmazie*, 1982, vol. 315, No. 5, pp. 474–476.
Lemini et al., "Synthesis of a Novel Asarone Dimer," *Organic Preparations and Procedures International*, 1981, vol. 13, No. 5, pp. 374–378.
Fomes et al., "Carbenium Ions Generated Upon Adsorption of 4–Methoxystyrenes Onto Acid Zeolites. A Kinetic Study," *Tetrahedron*, Elsevier Science Ltd., 1998, vol. 54, pp. 3827–3832.
Chai–Lin Kao et al., "A Novel Strategy for the Synthesis of Benzofuran Skeleton Neolignans: Application to Alianthoidol, XH–14, and Obovaten", *J. Org. Chem.*, 2002, vol. 67, pp. 6772–6787.
Alejandro Urzua et al., "2,5–Diaryl–3,4–Dimethyltetrahydrofuranoid Lignans", *Phytochemistry*, 1987, vol. 26, pp. 1509–1511.
Hiroko Shimomura et al., "Lignans from *Machilus Thunbergii*",*Phytochemistry*, 1987, vol. 26, No. 5, pp. 1513–1515.
*Journal of the American Chemical Society*, "Novel Nonphenol Oxidative Coupling", 1973, pp. 6861–6862.
Hiroe Kikuzaki et al., "Phenylbutanoid dimers from the leaves of *Alpinia flabellata*", *Phytochemistry*, 2001, vol. 56, pp. 109–114.
Uemura et al., "Thallium in Organic Synthesis. 46. Oxidative Coupling of Aromatic Compounds Using Thallium (III) Trifluoroacetate. Synthesis of Biaryls", *J. Org. Chem.*, 1977, vol. 42., pp. 764–765.
Eric Brown et al., "Synthesis of (±) Podorhizone via Intermediate α–Hydroxyalkylation of a β–Benzyl γ–Butyrolactone", *J.C.S. Chem. Comm.*, 1978, pp. 556–557.
LászióJuhász et al., Simple Synthesis of Benzofuranoid Neolignans from *Myristica fragans*. *J. Nat. Prod.*, 2000, vol. 63, pp. 866–870.
Robert S. Ward et al., "Lignans, neolignans and related compounds", *Nat. Prod. Rep.*, 1999, vol. 16, pp. 75–96.
Mohammed Taafrout et al., "Prestegane A, from *Steganotaenia araliacea* Hochst, : The First Natural Dibenzylbutanolide Lignan with a *meta*–Phenol—A Short Synthesis of *cis* and *trans* (±) Arctigenin –", *Tetrahedron Letters*, 1983, vol. 24, No. 31, pp. 3237–3238.
Shosuke Yamamura et al., "Three Novel Neolignans from *Heterotropa Takaoi* M.", *Tetrahedron Letters*, No. 49, pp. 4891–4894.
Chang Woo Lee et al., "Inhibition of Human Tumor Growth by 2'–Hydroxy– and 2'–Benzoyl–oxycinnamaldehydes", *Planta Medica*, 1999, vol. 65. pp. 263–266.
Clark W. Perry et al., "Synthesis of Lignans. I. Nordihydroguaiaretic Acid", *J. Org. Chem.*, 1972, vol. 37, No. 26, pp. 4371–4376.
Xiaochuan Chen et al., "A facile enantioselective approach to neolignans", *Tetrahedron: Asymmetry*, 2003, vol. 14, pp. 701–704.
Shigetoshi Kadoto et al., "Convenient Synthesis of Magnoshinin, an Anti–Inflammatory Neolignan", *Tetrahedron Letters*, 1987, vol. 28, No. 25, pp. 2857–2860.
Kaisa Syrjänen et al., "Regioselectivity in oxidative cross–coupling of phenols. Application to the synthesis of dimeric neolignans", *Tetrahedron*, 2001, vol. 57, pp. 365–370.
Wenxin Gu et al., "First asymmetric synthesis of chiral 1,4–benzodioxane lignans", *Tetrahedron Letters*, 2000, vol. 41, pp. 6079–6082.

* cited by examiner

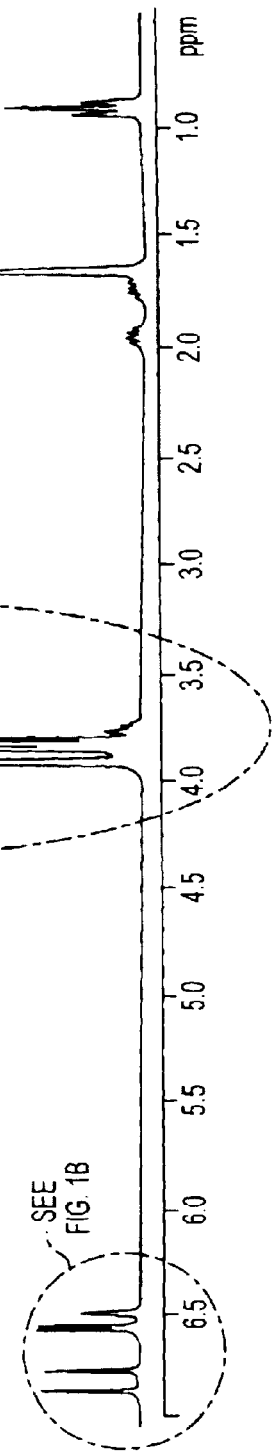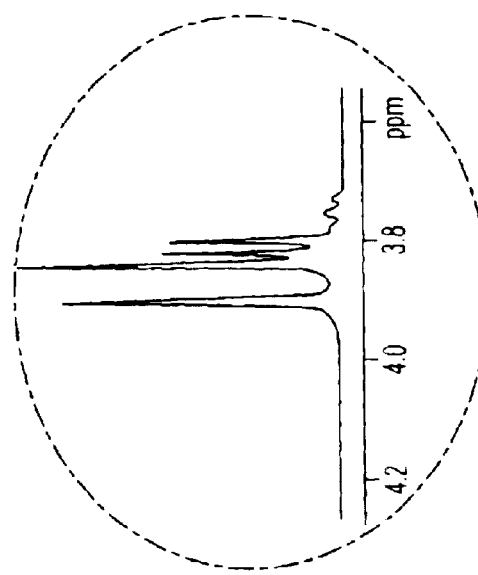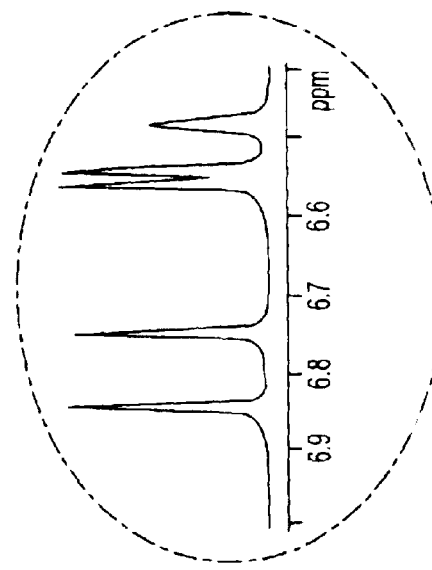

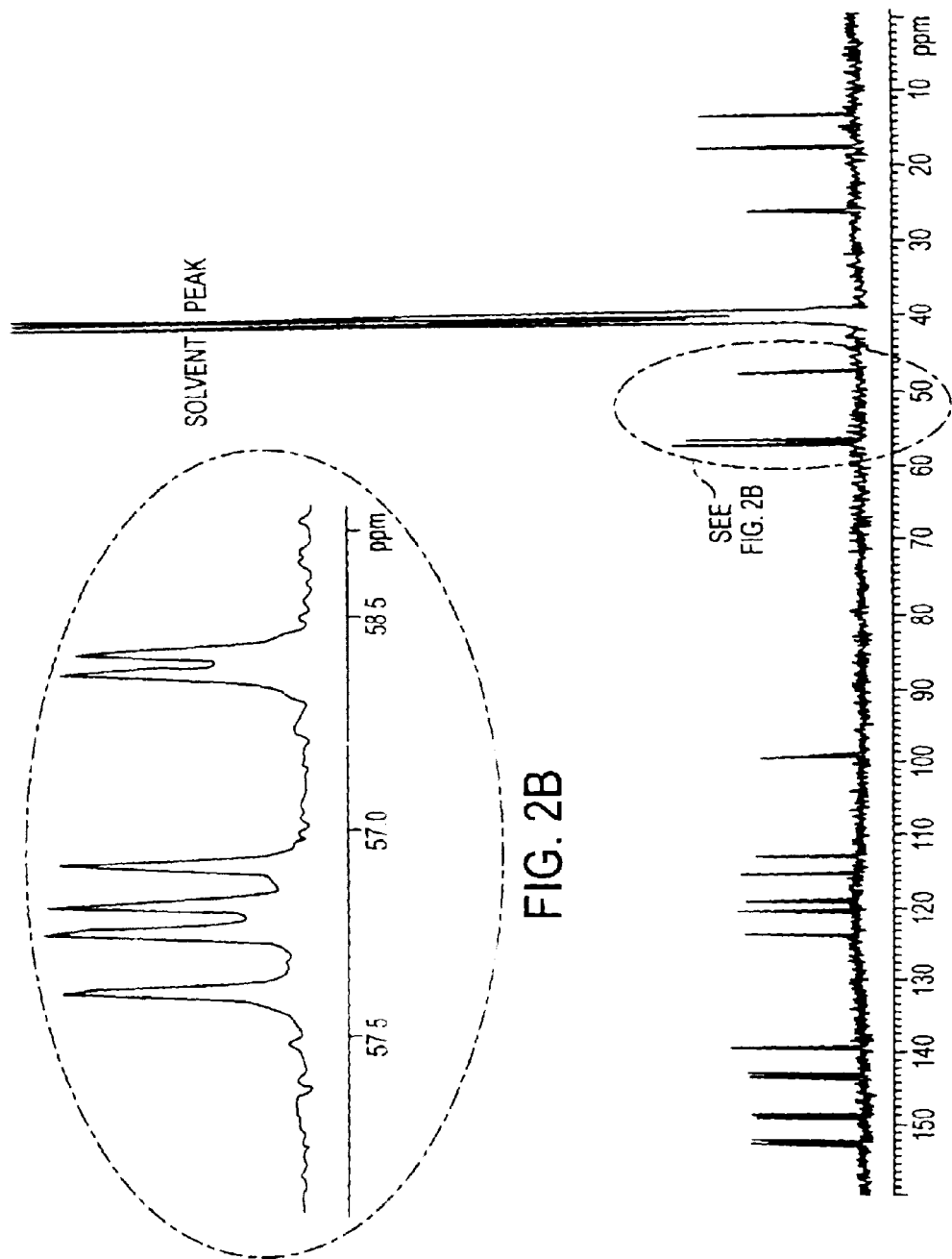

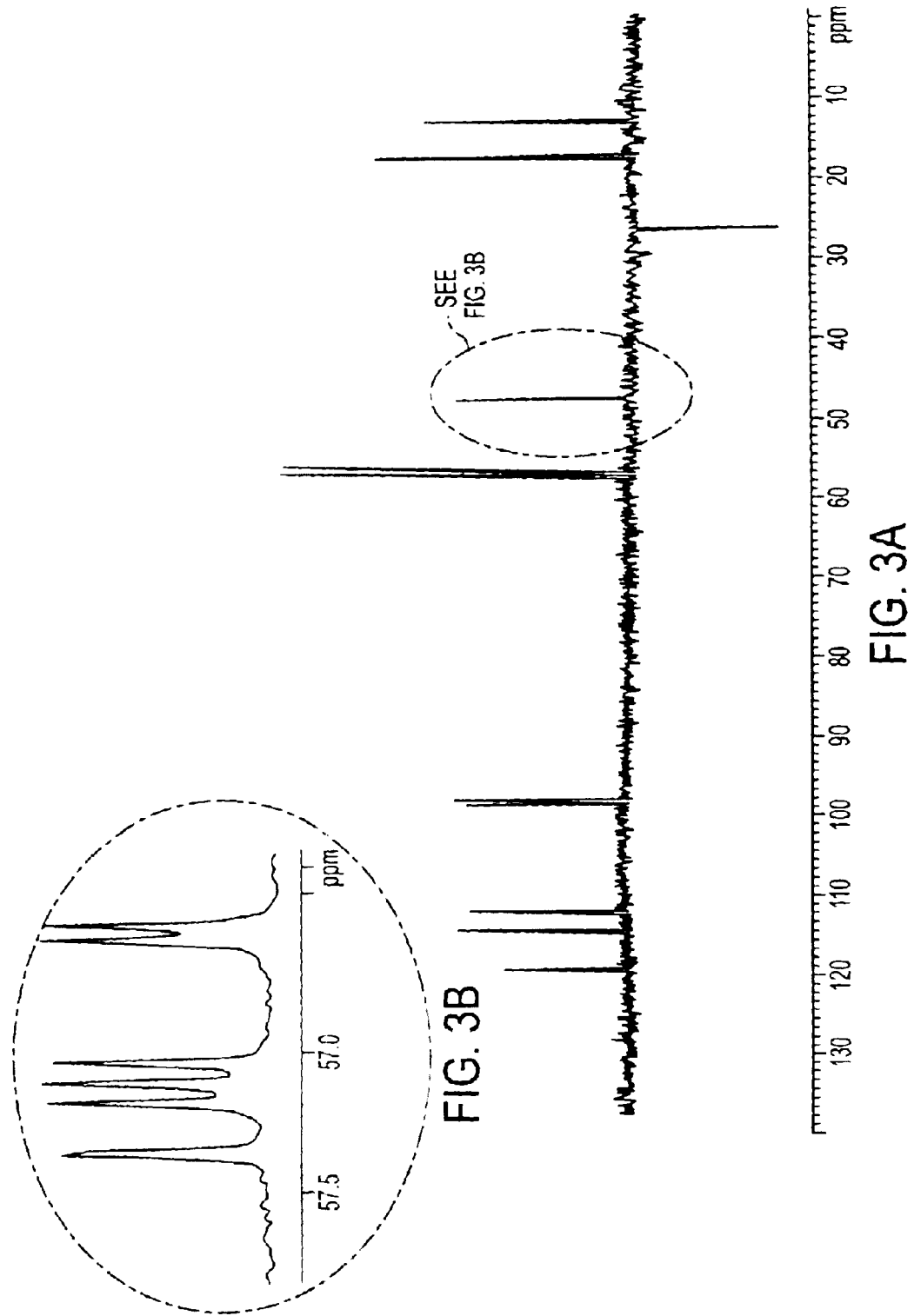

DDQ MEDIATED ONE STEP DIMERIZATION OF β-ASARONE OR β-ASARONE RICH *ACORUS CALAMUS* OIL IN THE FORMATION OF NOVEL NEOLIGNAN

CROSS-REFERENCE TO RELATED APPLICATIONS

The present application is a divisional application of U.S. application Ser. No. 10/108,269, filed Mar. 28, 2002 now abandoned, the contents of which are hereby incorporated by reference in their entirety.

FIELD OF THE INVENTION

The present invention relates to "DDQ mediated one step dimerisation of dihydro product of toxic β-asarone rich *Acorus calamus* oil towards formation of novel neolignan: 3-ethyl-2-methyl-3-(2",4",5"-trimethoxy)phenyl-1-(2',4',5"-trimethoxy) phenyl-1-propene" in which 2,4,5-trimethoxyphenylpropane (a dihydro product of asarone obtained via hydrogenation of β-asarone rich *Acorus calamus* oil) of the formula (I), undergoes dimerisation in a single step towards formation of neolignan 3-ethyl-2-methyl-3-(2',4",5"-trimethoxy)phenyl-1-(2',4',5'-trimethoxy)phenyl-1 propene (named as NEOLASA-I) of the formula II along with biologically active α-asarone and 1-(2,4,5-trimethoxy)phenyl-1-propanone as side products, thereof. Further, neolignan (NEOLASA-I) is hydrogenated to obtain its corresponding dihydro product 3-ethyl-2-methyl-3-(2",4",5"-trimethoxy)phenyl-1-(2',4',5'-trmethoxy)phenylpropane (named as NEOLASA-II) so as to confirm the structure as well as the position of double bond existing in the above parent neolignan (NEOLASA-I) which may additionally serve as a simple synthon towards preparation of naturally occurring rare neolignans (such as acoradin or magnosalin or heterotropan and phenyl indane derivative) and their artalogues in sufficient quantity to have opportunity for a wide range of biological activities including antifungal, antioxidant, antiinflammatory, neuroleptic, antihepatoxic, anticancer, anti-HIV and anti-PAF activities known for structurally similar neolignan derivatives (such as aurein or hexestrol or nordihydroguaiaretic acid derivatives etc.). In the present invention, the neolignan (NEOLASA-I) formation is the first example of DDQ assisted one step synthesis of neolignan, a dimer of phenylpropanoid, in good yield (32%) from 2,4,5-trimethoxyphenylpropane derivative.

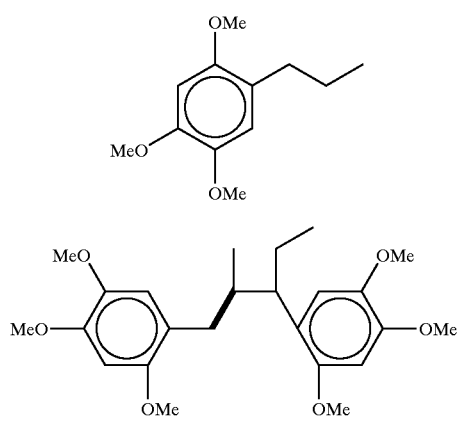

BACKGROUND OF THE INVENTION

Neolignans and lignans are known for their wide range of biological activities including hapatoprotective, hormone blocking, antibacterial, antifungal, plant growth regulator, anti-HIV, anticancer and antioxidant activities (Macrae, W. D. and Towers, G. H. N., Phytochemistry, 23 (6), 1207–1220 (1984); Ward, R. S., Tetrahedron, 46 (15), 5029–5041 (1990); Chariton, J. L., J. Nat. Prod., 61, 1447–1451 (1998); Alves, C. N.; Barroso, L. P.; Santos, L. S. and Jardim, I. N, J. Braz. Chem. Soc., 9(6), 577–582 (1998); Juhasz, L.; Dinya, Z.; Antus, S. and Gunda, T. E., Tetrahedron Letters, 41, 2491–2494 (2000); Tanaka, T.; Konno, Y.; Kuraishi, Y.; Kimura, I.; Suzuki, T. and Kiniwa, M., Biorg. & Med. Chem. Letts., 12, 623–627 (2002); U.S. Pat. Nos. 6,294,574; 6,201,016; 5.856,323; 5,639,782; 5,530,141; 4,704,462; 4,619,943 and 4,540,709; JP Patent No. 4082837; WO Patent No. 09215294 and EP Patent No. 159565)). Neolignans and lignans are a large group of natural products characterized by the coupling of two $C_6$–$C_3$ units which axe derived from cinnamic acid derivatives, however, both are present in traces in plants (Rao, K. V. and Rao, N. S. P., J. Nat. Prod., 53 (1), 212–215 (1990) and Filler, F.; Bail, J. C. L.; Duroux, J .L.; Simon, A. and Chulia, A. J., Planta Medica, 67, 700–704 (2001)). For nomenclature purposes, the $C_6$–$C_6$ unit is treated as propylbenzene and numbered from 1 to 6 in the benzene ring from 7 to 9 (or α to γ) starting from propyl group. With the second $C_6$–$C_6$ unit the numbers are primed. When the two $C_6$–$C_6$ units are linked by a bond between positions 8 and 8' (or β and β'), the compound is referred as a lignan. In the absence of the C-8 to C-8' (or β and β') bond, and where the two $C_6$–$C_3$ units are linked by a carbon-carbon bond, compound is referred to as neolignan. Dimers with linkages other than this type are known as cycloneolignan, epoxyneolignan and oxyneolignan etc. Similarly, the presence of a double bond (or triple bond) in the side chain (i.e. C-7 to C-9 or C-7 to C-9) of the lignan, neolignan or epoxyneolignan skeleton is indicated by changing the -ane ending to -ene (or -yne) with a locant to indicate the position of the double bond (Moss, G. P. Pure Appl. Chem., 72(8), 1493–1523 (2000)). The basic ring system of these neolignans and lignans can be deduced by dimerization of alilyl and p-propenylphenols (such as isoeugenol, coniferyl or sinapyl alcohol). Oxidation of phenols often yields phenoxy radicals, which couple with little selectivity. Both C—C and C—O bonds are formed, mainly in ortho- and para- positions to the phenolic hydroxyl. Synthetically useful reactions are obtained only when the reactivity is blocked by substituents in the aforementioned positions. For instance from 2,6- or 2,4-substituted phenols, C—C bonded biphenyls can be obtained in good yields. In other cases coupling can be directed by carrying out the reaction intramolecularly, ring closure being an effective way of inducing regioselectivity (Whitting, D. A. Oxidative Coupling of Phenols and Phenol Ethers. In Comprehensive Organic Synthesis, Trost, B. M.; Fleming, I.; Pattenden, G., Eds.; Pergemon: Oxford, Vol. 3, 659–703 (1991)). Similarly, oxidation of a mixture of two phenols can lead to a mixture of dimers of the individual phenols and cross-coupling products between the different phenols. When one phenol reacts much faster than the other, for instance if it has a lower oxidation potential, it tends to dimerize without formation of significant amounts of cross-coupling products (Syrjanen, K. and Brunow, G., J. Chem. Soc. Perkin Trans 1, 3425–3429 (1998)). One approach to this problem is to start with the less reactive phenol in large excess, and continuously add the more reactive phenol (and the oxidant) at a rate which is slow enough to keep its concentration too low for significant dimerisation. But this method is cumbersome and leads to a large reaction volumes, and is also difficult to reproduce. A wide range of oxidants such as $K_3Fe(CN)_6$, $H_2O_2$, $FeCl_3$, $VOF_3$, thallium (III) tristrifluoacetate, horseradish peroxidase, iodobenzene diacetate (Frank, B. and Schlingloff, G., Liebig. Ann. Chem., 659, 132 (1962); Taylor, W. I. and Battersby, A. R. In "Oxidative Couplings of Phenols", Marcel Dekker, N.Y. (1967); Kametani, T. and Fukumoto, K., Synthesis, 657 (1972); Taylor, E. C.; Andrade, J. G.; Rall, G. J. H. and McKillop, A., J. Am. Chem. Soc., 93, 4841 (1971); Kaisa, S. and Gösta, B., Tetrahedron, 57,365–370 (2001); Juhaasz, L.; Kfürti, L. and Antus, S., J. Nat. Prod, 63, 866–870 (2000)) and many others have been used for oxidative coupling but generally these reagents gave poor yield, and often complex mixtures. Indeed, phenoxy radical or phenoxonium ion intermediate is most common for synthesis of lignans and neolignans but there are a few patents and papers where non-phenolic compounds have been used for the synthesis of lignans and neolignans (Kadota, S.; Tsubono, K. and Makino, K., Tetrahedron Letters, 28 (25), 2857–2860 (1987) and Dhal, R.; Landais, Y.; Lebrun, A.; Lenain, V. and Robin, J. P., Tetrahedron, 50(4), 1153–1164 (1994)). For example, nordihydroguaiaretic acid (one of the most important dimer derived from resinous exudates of many plants), associated with a wide range of pharmacological activities, including the inhibition of the human papillomavirus, herpes simplex, HIV and hyperglycemic activity, has been synthesized by dimerization of non-phenolic compounds such as dimethoxypropiophenone (Perry, C. W. U.S. Pat. No. 3,769,350 (1975)), substituted benzylmagnesium chloride (Akio, M.; Kohei, T.; Keizo, S. and Makoto, K. Tetrahedron Letters, 21,4017–4020 (1980)) and dimethoxyphenylacetone (Mikail, H. G. and Barbara, N. T. Tetrahedron Letters, 42, 6083–6085 (2001)). However, above methods have a number of disadvantages including special handling of reagents, maintaining temperature below zero degree, expensive reagents and overall low yield, hence, none of the synthetic methods can be scaled up for industrial exploitation. On the contrary, the present invention is free from above drawbacks and discloses one step dimerisation of 2,4,5-trimethoxyphenylpropane (a dihydro product of asarone obtained via hydrogenation of β-asarone rich *Acorus calamus* oil) of the formula I (Example I) into novel neoliguan 3-ethyl-2-methyl-3-(2'',4'',5''-trimethoxy)phenyl-1-(2',4',5'-trimethoxy)phenyl-1-propene (named as NEOLASA-I) of the formula II (Example II). Further, neolignan (NEOLASA-I) is hydrogenated to obtain its corresponding dihydro product (3-ethyl-2-methyl-3-(2'',4'',5''-trimethoxy) phenyl-1-(2',4',5'-trimethoxy) phenylpropane) (named as NEONLASA-II) (Example III) so as to confirm the structure as well as to determine the position of double bond existing in the above parent neolignan (NEOLASA-I) of the formula (II) which may additionally serve as a simple synthon towards preparation of naturally occurring rare neolignans (such as acoradin or magnosalin or heterotropan and phenyl indane derivative) and their analogues in sufficient quantity to have opportunity for a wide range of biological activities (Wenkert, E.; Gottlieb, H. E.; Gottlieb, O. R.; Pereira, M. O. D. S. and Formiga, M. D., Phytochemistry, 15, 1547–1551 (1976); Kikuchi, T.; Kadota, S.; Yanada, K.; Tanaka, K.; Watanabe, K.; Yoshozaki, M.; Yokoi, T. and Shingu, T., Chem. Pharm. Bull. 31, 1112 (1983); Yamamura, S.; Niwa, M.; Nonoyama, M. and Terada, Y. Tetrahedron Letters, 4891 (1978); Kadota, S.; Tsubono, K.; Mokino, K.; Takeshita, M. and Kikuchi, T., Tetrahedron Letters, 28 (25), 2857–2860 (1987); Shimomura, H.; Sashida, Y and Oohara, M., Phytochemistry, 26(5), 1513–1515 (1987); Ahn, B.T.; Lee, S.; Lee, S. B.; Lee, E. S.; Kim, J. G. and Jeong, T. S., J. Nat. Prod., 64, 1562–1564 (2001) and Filleur, F.; Le Bail, J. C.; Duroux, J. L.; Simon, A. and Chulia, A. J., Planta Medica, 67, 700–704 (2001)).

In fact, formation of neolignan was observed accidentally when we were interested to develop a simple and economical process for the preparation of α-asarone, a well known hypolipideamic and antiplatelet active phenylpropanoid (Hernandez, A.; Lopez, M. L.; Chamorro, G. and Mendoza, F. T., Planta Medica, 59 (2), 121–124 (1993); Garduno, L.; Salazar, M.; Salazar, S.; Morelos, M. E.; Labarrios, F.; Tamariz, J. and Chamorro, G. A., J. of Ethnopharmacology, 55 (2), 161–163, (1997) and (Janusz, P.; Bozena, L.; Alina, T. D.; Barbara, L.; Stanislaw, W.; Danuta, S.; Jacek, P.; Roman, K.; Jacek, C.; Malgorzata, S. and Zdzislaw, C., J. Med. Chem., 43, 3671–3676 (2000)), via treatment of 2,4,5-trimethoxyphenylpropane of the formula I with DDQ in acetic acid into 1-(2,4,5-trimethoxy)phenyl-1-acetoxypropane followed by alkaline hydrolysis and its acidic dehydration to obtain α-asarone. This concept was based upon the reported method wherein treatment of benzylic compound with $Hg(OAC)_2$/AcOH or DDQ/AcOH provided corresponding acetate derivative (Rao, K. V. and Chattopadhyay, S. K., Tetrahedron, 43, 669 (1987) and Rao, K. V. and Rao, N. S. P., J. Nat. Prod. 53(1), 212–215 (1990)). But to our surprise, the treatment of 2,4,5-trimethoxyphenylpropane (benzylic compound) with DDQ (1.0–1.3 moles) in the presence of acetic acid, provides mixture of unexpected products namely neolignan (32% yield), α-asarone (9% yield) and 1-(2,4,5-trimethoxy)phenyl-1-propanone (22% yield) (Example II) without formation of expected 1-phenyl-1-aceoxypropane derivative (Subodh, K. J. Org. Chem. 50, 3070–3073 (1985) and Ward, R. S. Tetrahedron Letters, 48 (15), 5029–5041 (1990)). The structure of neolignan (3-ethyl-2-methyl-3-(2'',4'',5''-trimethoxy)phenyl-1-(2',4',5'-trimethoxy)phenyl-1-propene or 2,2',4,4',5-5'-hexamethoxy-7',8-neolig-7-ene), α-asarone and 1-(2,4,5-trimethoxy)phenyl-1-propanone (or isoacoramone) are successfully confirmed on the basis of spectral data (Example II). The formation of all the three products are postulated only when a part of 2,4,5-trimethoxyphenylpropane ($C_6$–$C_3$) undergoes dehydrogenation with DDQ towards formation of α-asarone while little other part of 2,4,5-trimethoxyphenylpropane undergoes oxidation with DDQ for isoacoramone formation. However, neolignan formation is possible only if some part of initially formed α-asarone undergoes rearrangements with unreacted 2,4,5-trimethoxyphenylpropane and DDQ towards dimerisation. Further, detailed mechanistic studies for above products are in progress. It is worthwhile to mention that increase in the amount of DDQ (1.4–2.1 moles) in acetic acid gave once again neolignan (NEOLASA-I) and α-asarone but 1-(2,4,5-trimethoxyphenyl)-1-propanone in little higher yield (39%) than above (22%) (Example II). Later on, like α-asarone, isoacoramone (2,4,5-trimethoxypropiophenone) is also realized as an interesting rare phenylpropanoid occurring in well known medicinal plants *Acorus calamus, Piper marginatum* as well as in *Acorus tararinowii* but only in traces (Mazza, G., J. of Chromatography, 328, 179–206 (1985); Santos, B. V. de O. and Chaves, M. C. de O., Biochem. Systematics Ecology, 25, 539–541 (1999) and Jinfeng, Hu and Xiaozhang, Feng, Planta Medica, 66, 662–664 (2000).

In conclusion, our invention discloses a simple and economical process for preparing novel neolignans (3-ethyl-2-methyl-3-(2",4",5"-trimethoxy)phenyl-1-(2',4',5'-trimethoxy)phenyl-1-propene of the formula (II) and 3-ethyl-2-methyl-3-(2",4",5"-trimethoxy)phenyl-1-(2',4',5'-trimethoxy)phenylpropane of the formula (III) along with α-asarone of formula (IIa), and isoacaromone (2,4,5-trimethoxypropiophenone) of formula (IIb), as side products thereof, starting from relatively cheaper and economical material 2,4,5-trimethoxyphenylpropane obtained via hydrogenation of β-asarone rich *Acorus calamus* oil as outlined in Scheme-I. Other objectives and advantages of the present invention will be made apparent as the description progresses.

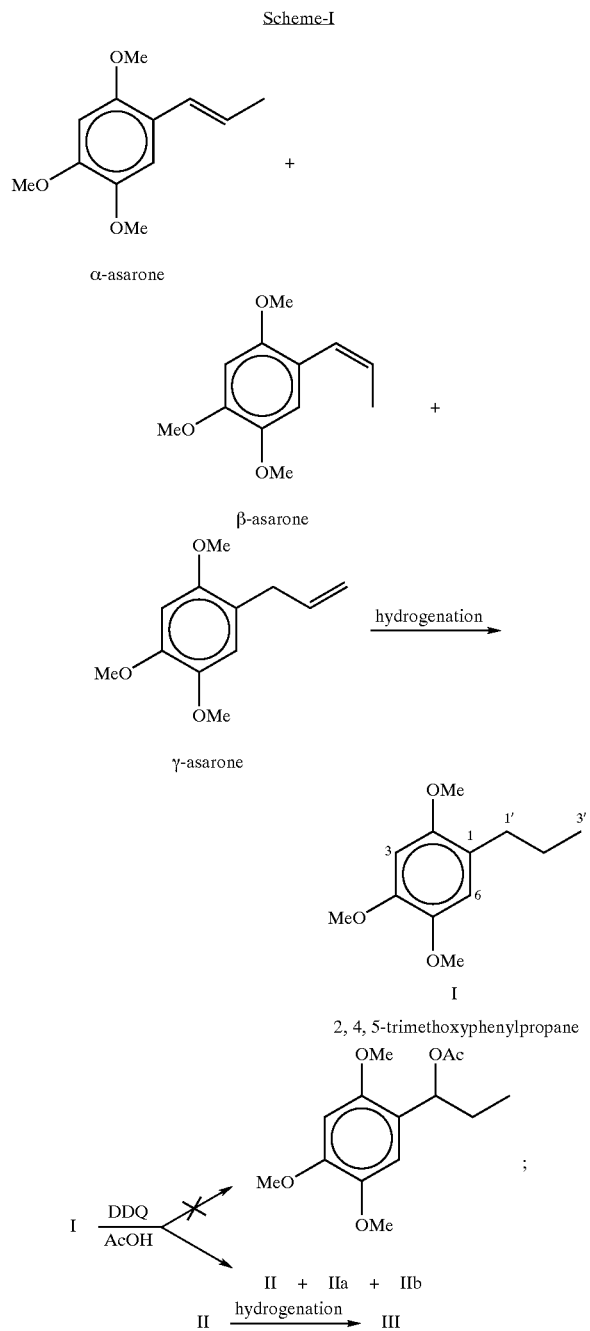

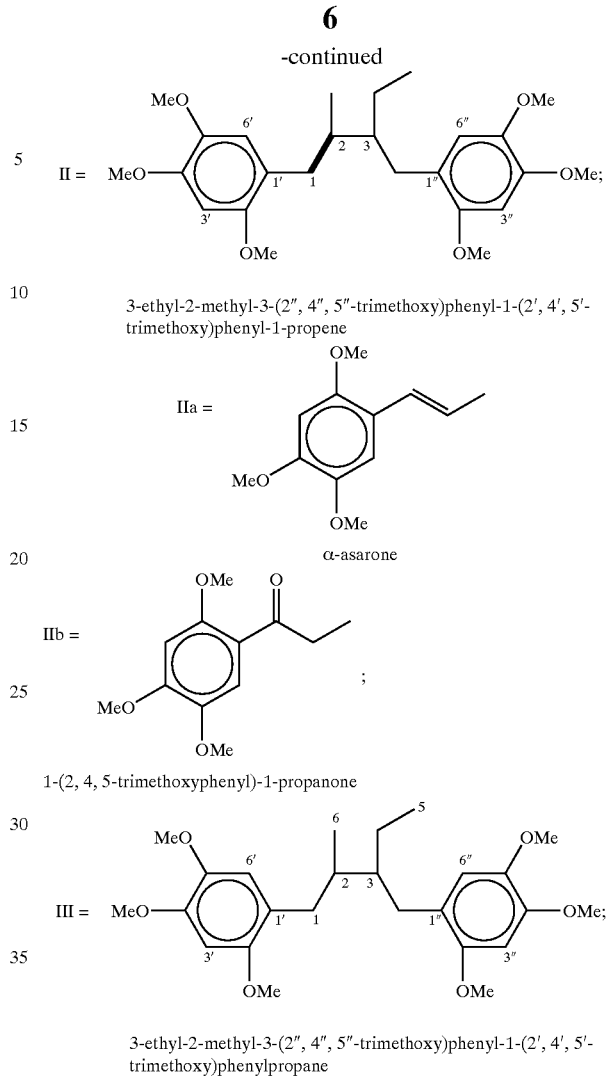

OBJECTIVES OF THE INVENTION

The main object of the present invention is to prepare 3-ethyl-2-methyl-3-(2",4",5"-trimethoxy)phenyl-1-(2',4',5'-trimethoxy)phenylpropene, a neolignan, from 2,4,5-trimethoxyphenylpropane which is, in fact, the hydrogenated product of toxic β-asarone isolated from commercially available *Acorus calamus* oil.

Another object of the present invention is to utilize toxic β-asarone rich calamus oil of tetraploid or hexaploid varieties (distributed extensively in Asian countries), thereby, enhancing the profitable use thereof.

Still another object of the invention is to study the interaction of 2,4,5-trimethoxyphenylpropane by varying amount of DDQ, time and temperature.

Yet another object of the invention is to develop easy purification process to obtain high purity of neolignan and side products.

Yet another object of the invention is to establish the structure of side products which finally appeared to be a naturally occurring rare phenylpropanoids namely α-asarone and 1-(2,4,5-trimethoxy)phenyl-1-propanone.

Yet another object of the invention is to further establish the position of the double bond existing in the above neolignan by its reduction into corresponding dihydro neolignan i.e. 3-ethyl-2-methyl-3-(2",4",5"-trimethoxy)phenyl-1-(2',4',5'-trimethoxy)phenylpropane.

SUMMARY OF THE INVENTION

The present invention provides a process for the preparation of neolignan utilizing a mild and efficient reagent 2,3-dichloro-5,6-dicyano-1,4-benzoquinone (DDQ) and 2,4,5-trimethoxyphenylpropane which is, in fact, the hydrogenated product of toxic β-asarone isolated from commercially available calamus oil. It is worthwhile to mention that the above process not only led to novel neolignan (3-ethyl-2-methyl-3-(2",4",5"-trimethoxy)phenyl-1-(2',4',5'-trimethoxy)phenyl-1-propene) (named as NEOLASA-I) but also provided two more products which later on were characterized as biologically active, rare, naturally occurring phenylpropanoids namely, α-asarone and 1-(2,4,5-trimethoxyphenyl)-1-propanone (isoacoramone). Further, the structure of neolignan (NEOLASA-I) was established by its catalytic hydrogenation into corresponding dihydro neolignan (3-ethyl-2-methyl-3-(2",4",5"-trimethoxy)phenyl-1-(2',4',5'-trimethoxy)phenylpropane) (named as NEOLASA-II). As per literature survey, neolignans are found to be interesting dimeric product of phenylpropanoids having a wide range of activities such as antioxidant, anti-cancer and anti-HIV but are present only in traces in the plant kingdom. Keeping in view its wide scope, several partial and total synthesis of neolignans have been developed but most of the methods require expensive starting materials and reagents and also proceed in multisteps with overall poor yield. Therefore, our finding and disclosure of neolignan formation during DDQ assisted oxidation of 2,4,5-trimethoxyphenylpropane in one step process, is a cheaper and economical method than so far reported methods, as well as, our invention is capable of forming a series of biologically active neolignan derivatives.

BRIEF DESCRIPTION OF THE ACCOMPANYING DRAWINGS

FIGS. 1A–1C are $^1$H NMR (300 MHz) spectra of 3-ethyl-2-methyl-3-(2", 4", 5"-trimethoxy)phenyl-1-(2', 4', 5'-trimethoxy)phenyl-1-propene (in CDCl$_3$) of the reaction product of Example II.

FIGS. 2A–2B are $^{13}$C NMR (75.4 MHz) spectra of 3-ethyl-2-methyl-3-(2",4",5"-trimethoxy)phenyl-1-(2',4',5'-trimethoxy)phenyl-1-propene (in CDCl$_3$) of the reaction product of Example II.

FIGS. 3A–B are DEPT-135° spectra of 3-ethyl-2-methyl-3-(2",4",5"-trimethoxy)phenyl-1-(2',4',5'-trimethoxy)phenyl-1-propene (in CDCl$_3$) of the reaction product of Example II.

Figure 4:
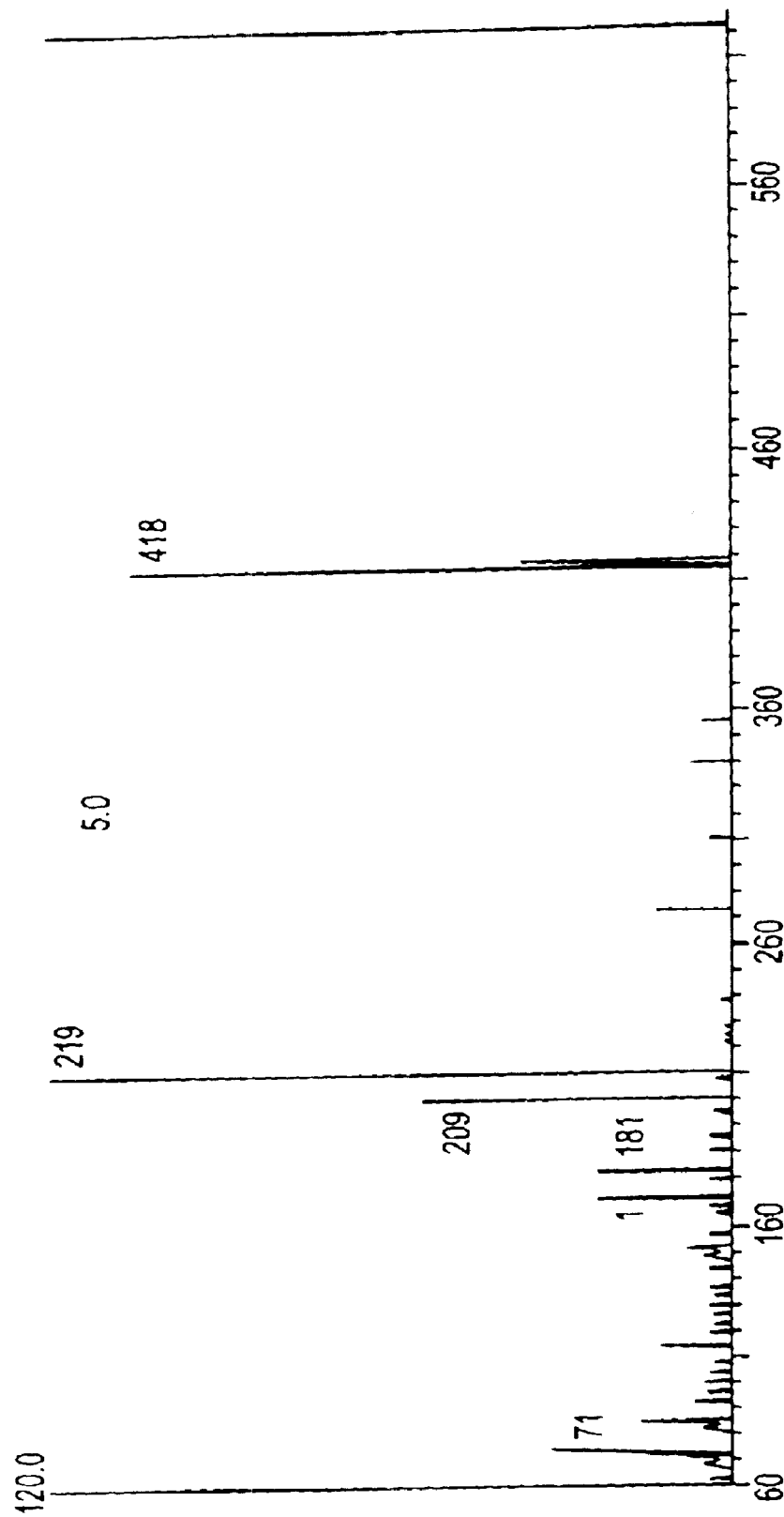
Figure 5:
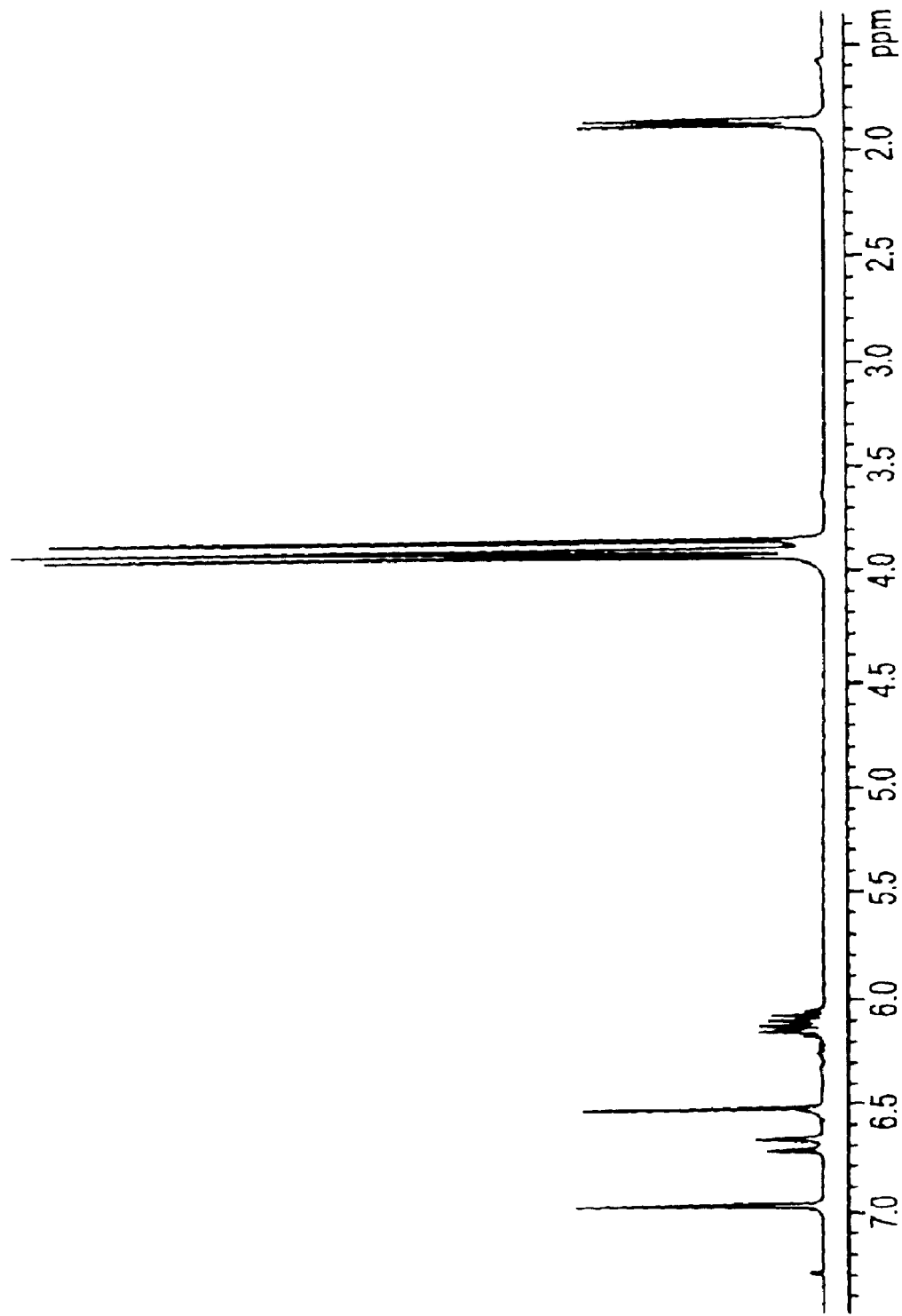
Figure 6:
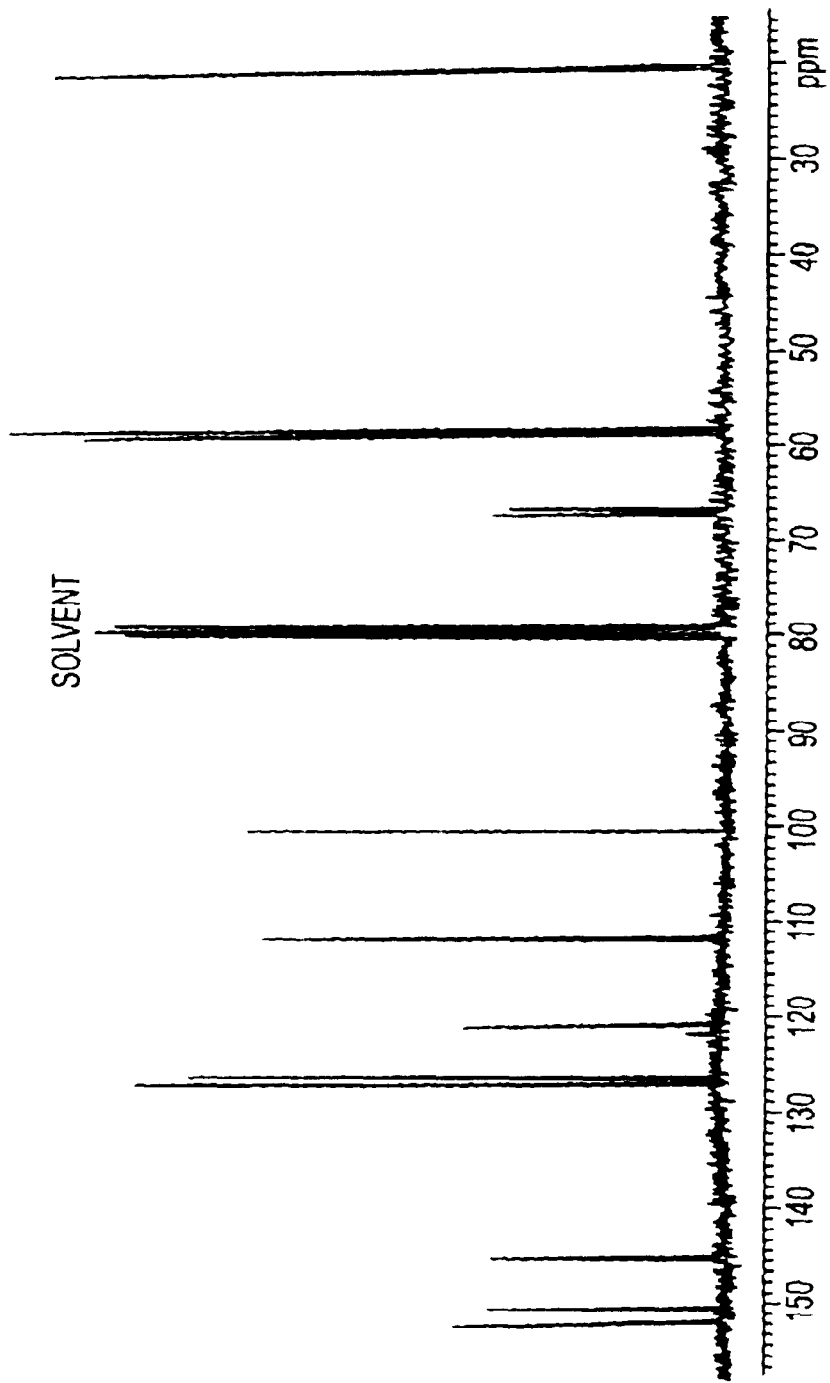
Figure 7:
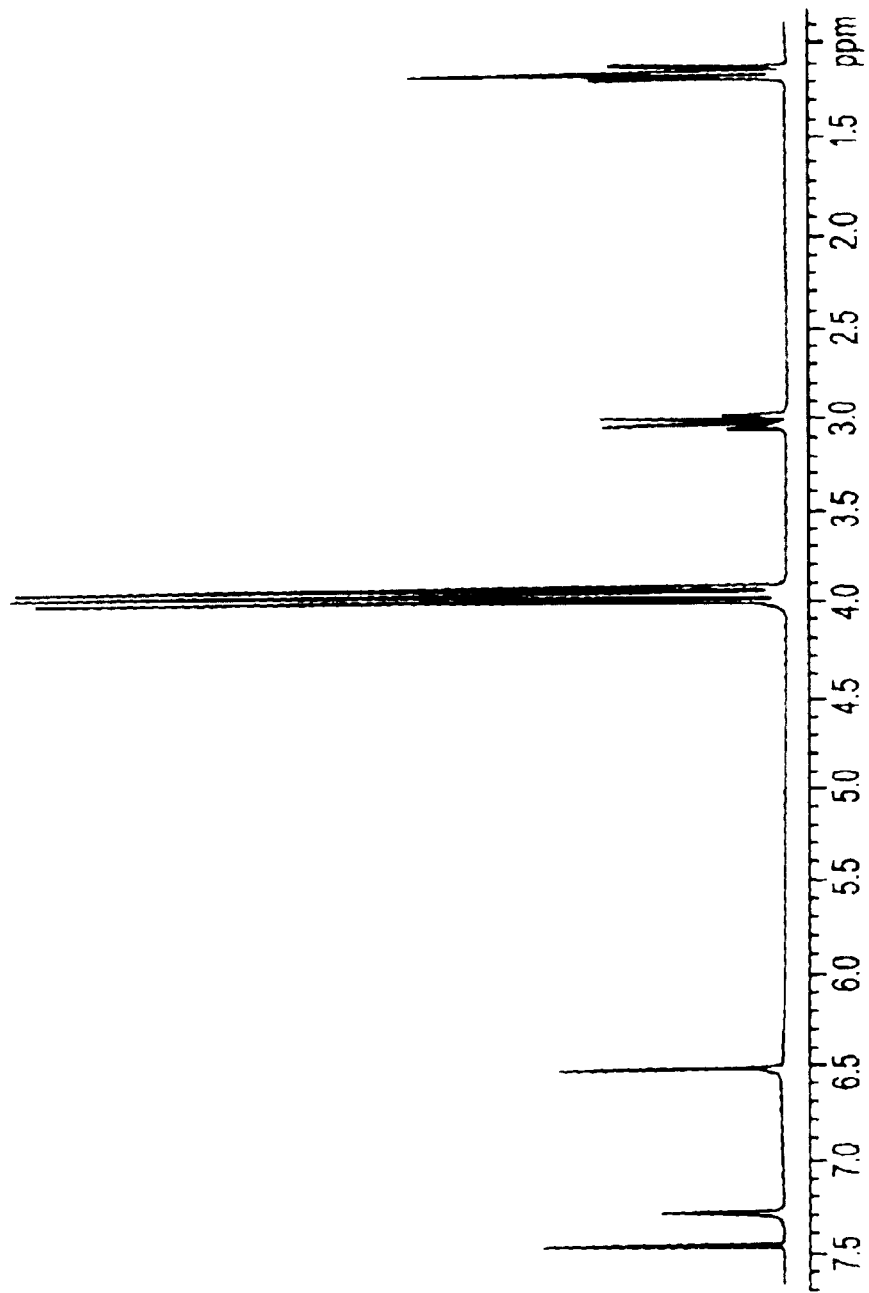
Figure 8:
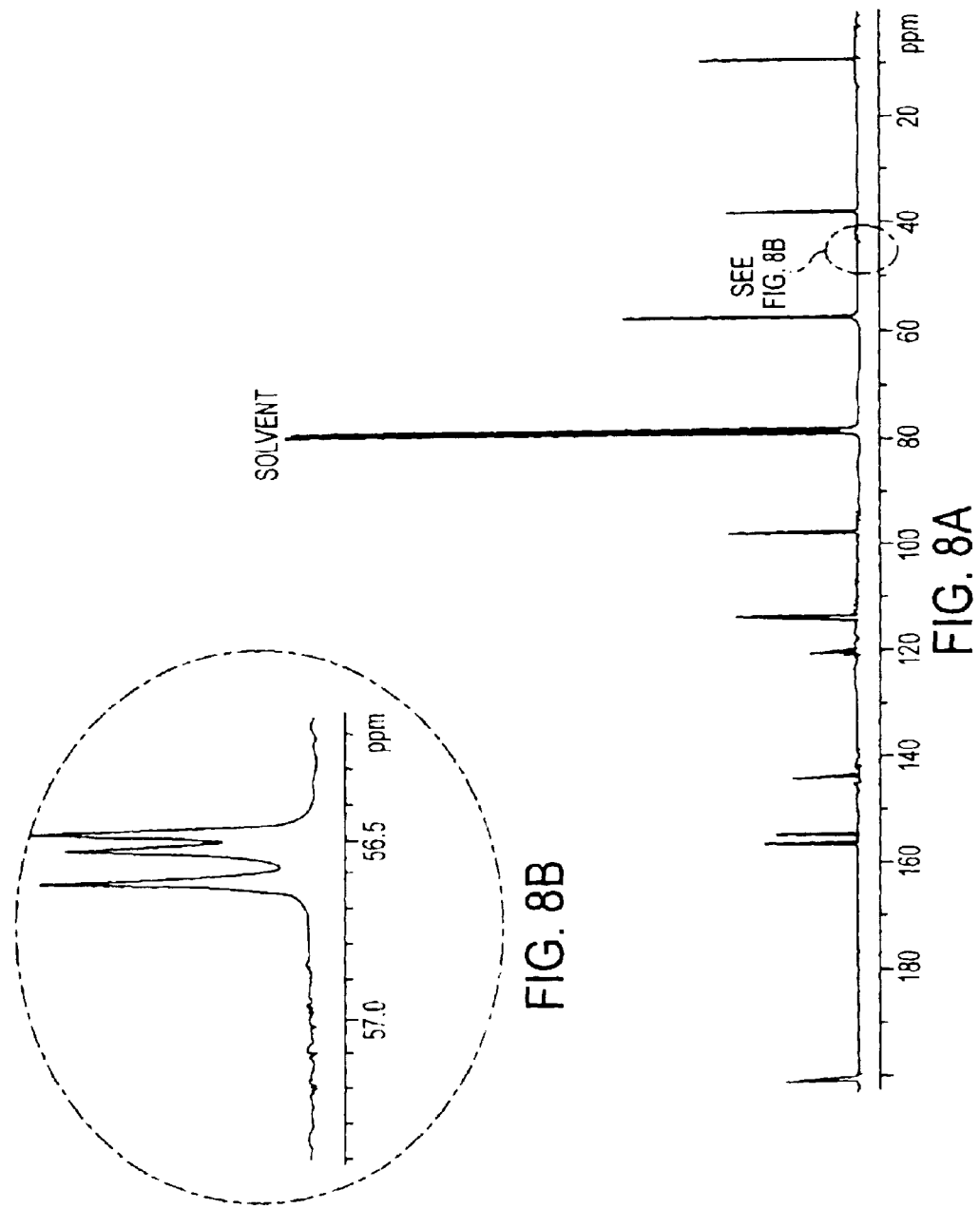

FIG. 4 is the electro spray (ES) mass spectrum of 3-ethyl-2-methyl-3-(2",4",5"-trimethoxy)phenyl-1-(2',4',5'-trimethoxy)phenyl-1-propene (Mw 416) of the reaction product of Example II FIG. 5 is $^1$H NMR (300 MHz) spectra of α-asarone (in CDCl$_3$) of the reaction product of Example II FIG. 6 is $^{13}$C NMR (75.4 MHz) spectra of α-asarone (in CDCl$_3$) of the reaction product of Example II FIG. 7 is $^1$H NMR (300 MHz) spectra of 1-(2,4,5-trimethoxy)phenyl-1-propanone (in CDCl$_3$) of the reaction product of Example II FIGS. 8A–B are $^{13}$C NMR (75.4 MHz) spectra of 1-(2,4,5-trimethoxy)pheny-1-propanone (in CDCl$_3$) of the reaction product of Example II.

Figure 9:
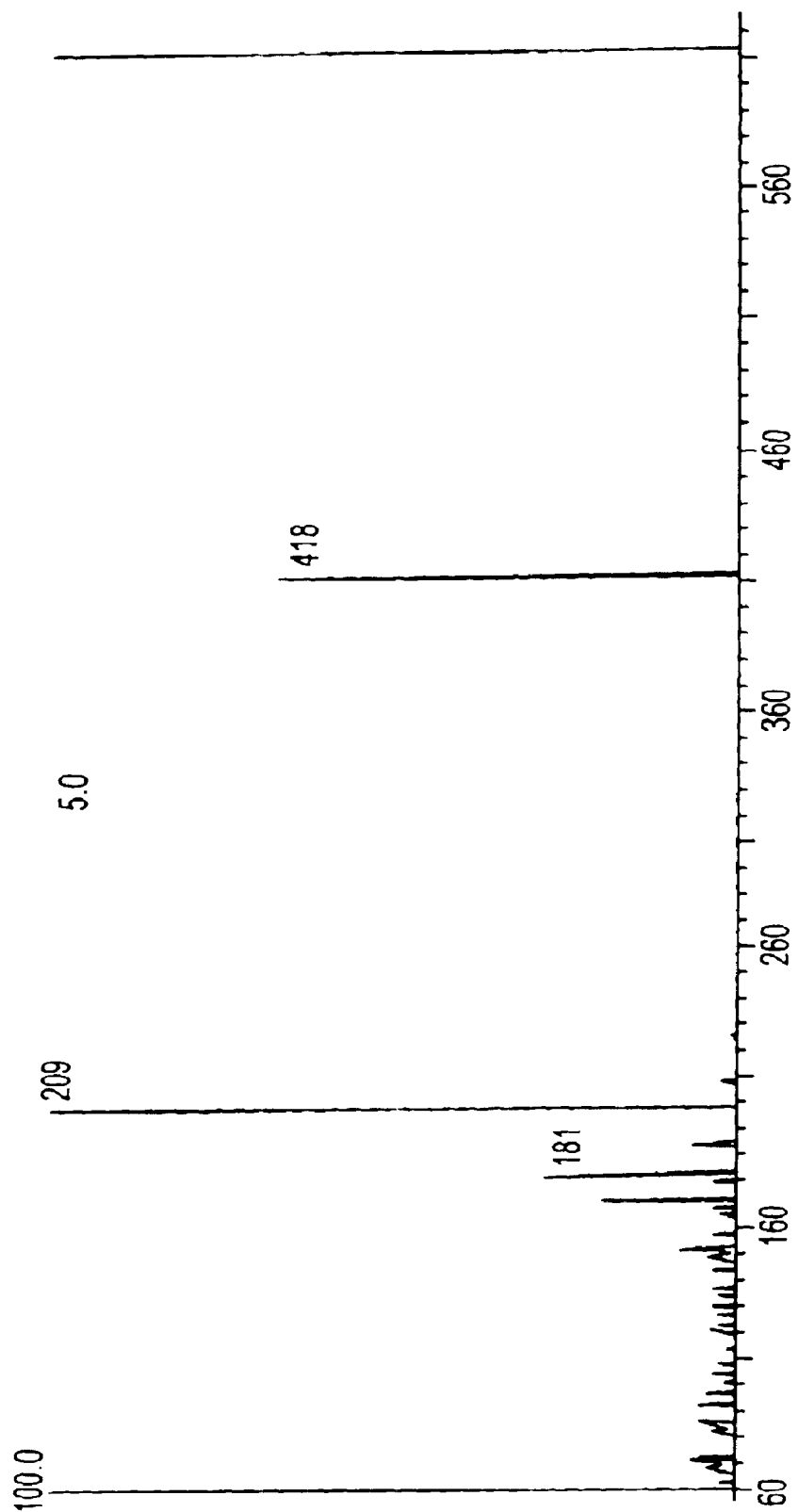

FIG. 9 is the electro spray (ES) mass spectrum of 3-ethyl-2-methyl-3-(2",4",5"-trimethoxy)phenyl-1-(2',4',5'-trimethoxy)phenyl-1-propene (MW 418) of the reaction product of Example III

DETAILED DESCRIPTION OF THE INVENTION

Accordingly, the present invention provides "DDQ mediated one step dimerisation of dihydro product of toxic β-asarone rich *Acorus calamus* oil in the formation of novel neolignan: 3-ethyl-2-methyl-3-(2",4",5"-trimethoxy)phenyl-1-(2',4',5'-trimethoxy)phenyl-1-propene" wherein the said process comprises hydrogenation of toxic β-asarone or calamus oil containing mixture of α,β- and γ-asarone to obtain 2,4,5-trimethoxyphenylpropane of formula I followed by reacting the above said compound with DDQ at a temperature in the range of 5–120° C. for a period ranging from 30 minutes to 72 hours using acetic acid as solvent to obtain 3-ethyl-2-methyl-3-(2",4",5"-trimethoxy)phenyl-1-(2',4',5'-trimethoxy)phenyl-1-propene and side products thereof.

In an embodiment of the present invention, a simple process is available to prepare neolignan from 2,4,5-trimethoxyphenylpropane, which is, in fact, the hydrogenated product of toxic β-asarone isolated from commercially available calamus oil.

In another embodiment of the present invention, a simple process is available for the commercial utilization of internationally banned but widely available toxic β-asarone from *Acorus calamus* oil of tetraploid or hexaploid varieties (distributed extensively in Asian countries), thereby, enhancing the profitable use thereof.

In still another embodiment of the present invention, a simple process involves the conversion of mixture of all the three isomeric forms of phenylpropene i.e. α,β and γ-asarone firstly into 2,4,5-trimethoxyphenylpropane and then utilizing it as a simple synthon for the preparation of 3-ethyl-2-methyl-1-(2',4',5'-trimethoxy)-phenyl)-3-(2",4", 5"-trimethoxy)phenyl-1-propene and side products α-asarone and 1-(2,4,5-trimethoxy)phenyl-1-propanone thereof.

In yet another embodiment of the present invention, a simple process which discloses the interaction of 2,4,5-trimethoxyphenylpropane with varying amount of DDQ and time, temperature and solvents.

In yet another embodiment of the present invention, the molar ratio of DDQ to 2,4,5-trimethoxyphenylpropane is in the range of 2.1:1.0 to 1.0:1.0.

In yet another embodiment of the present invention, provides an easy purification process to obtain neolignan and side products in high purity.

In yet another embodiment of the present invention, provides novel neolignan in sufficient quantity via simple and economical route, which further provides the opportunity for the evaluation of its wide range of biological activities known for structurally similar neolignans.

In yet another embodiment of the present invention, provides novel neolignan as a crystalline solid with melting point ranging from 96°–97C.

In yet another embodiment of the present invention, provides novel neolignan having one asymmetric center.

In yet another embodiment of the present invention provides novel neolignan, this is capable of undergoing conversion into several naturally occurring neolignan and lignan derivatives.

In yet another embodiment of the present invention, provides novel dihydro neolignan i.e. 3-ethyl-2-methyl-3-

(2",4",5"-trimethoxy)phenyl-1-(2',4',5'-trimethoxy) phenylpropane (NEOLASA-II) obtained by catalytic hydrogenation of 3-ethyl-2-methyl-3-(2",4",5"-trimethoxy) phenyl-1-(2',4',5'-trimethoxy)phenyl-1-propene (NEOLASA-I).

In yet another embodiment of the present invention, provides a novel dihydro (NEOLASA II) which is capable of undergoing conversion into several naturally occurring neolignan and lignan derivatives.

In yet another embodiment of the present invention provides a novel dihydro neolignan in sufficient quantity via simple and economical route, thus, providing an opportunity for its biological evaluation.

In yet another embodiment of the present invention provides novel dihydro neolignan having two asymmetric centers.

Although the plant derived products have found widespread applications in the field of essential oils, colours and dyes, cosmetics, pharmaceuticals and in many others, not only because they are easily available and are cheaper but also an important reason has been the notion that they are safer than synthetic products, which may not always be true. There are several phytochemicals which beyond a certain limit, diminishes the market potential of products such as phenylpropanoids rich essential oils which get deteriorated specifically by few isomeric forms of phenylpropenes (Miller, E. C.; Swanson, A. B.; Phillips, D. H.; Fletcher, T. L.; Liem, A. and Miller, J. A., Cancer Research, 43 (3), 1124–1134 (1983); Kim; S. C.; Liem; A.; Stewart; B. C. and Miller, J. A. Carcinogensis, 20 (7), 1303–1307 (1999) and Lazutka, J. R.; Mierauskiene, S. and Dedonyte, V. Food & Chemical Technology, 39, 485–492 (2001)). Generally, trans-isomers (e.g. α-asarone and isoeugenol etc) are found safer for human consumption while cis/allyl-isomers (e.g. β-asarone and saffrole) are found toxic and carcinogenic (Harborne, J. B. and Baxter, H., Phytochemical Dictionary: A Handbook of Bioactive Compounds from Plants, Taylor & Francis Ltd., Washington D.C., 474 (1993)). As a result, the most affected oil is *Acorus calamus* (family: Araceae) oil in which tetraploid and hexaploid varieties (distributed extensively in Asian countries like India, Japan, Pakistan and China) contain very high percentage of cis-phenylpropene i.e. β-asarone (varying from 70 to 90%) while diploid and triploid varieties contain limited amount of β-asarone (3 to 8%) (Stahl, E. and Keller, K.; Planta Medica 43, 128–140 (1981); Waltraud, G. and Schimmer, O., Mutation Research 121, 191–194 (1983); Mazza, G., J. of Chromatography, 328, 179–206 (1985); Motley, T. J., Economic Botany, 48, 397–412 (1994)).

β-asarone is experimentally proved to be carcinogenic in animals and has also been found to induce tumors in the duodenal region after oral administration. In addition, β-asarone has also shown chromosome damaging effect on human lymphocytes in-vitro after metabolic activation (Taylor, J. M.; Jones, W. I.; Hogan, E. C.; Gross, M. A.; David, D. A. and Cook, E. L., Toxicol. Appl. Pharmacol., 10, 405 (1967); Keller, K.; Odenthal, K. P. and Leng, P. E., Planta Medica 1, 6–9 (1985); Abel, G., Planta Medica, 53(3), 251–253 (1987) and Riaz, M.; Shadab, Q.; Chaudhary, F. M., Hamdard Medicus, 38(2), 50–62 (1995)). As a result, the calaxiius oil of Asian origin is internationally banned for any kind of use in flavor, perfumery and pharmaceutical industries. To the best of our knowledge, there is no report in which toxic β-asarone of calamus oil is utilized for its value addition except very recently by our group (Sinha, A. K.; Dogra, R. and Joshi, B. P., md. J. Chem., 41B, (2002) (in press); Sinha, A. K.; Joshi, B. P. and Dogra, R., Nat. Prod. Left., 15(6), 439–444 (2001); Sinha, A. K.; Acharya, R. and Joshi, B. P., J. Nat. Prod. (2002) (in press), Sinha, A. K.; Dogra, R. and Joshi, B. P., Sinha, A. K.; Joshi, B. P., and Dogra, JP patent application No. 2001.68716 filed on 12 Mar. (2001); Sinha, A. K.; Joshi, B. P., and Dogra, U.S. patent application Ser. No. 09-805,832 filed on 14 Mar. (2001) and U.S. patent application Ser. No. 09-823,123 filed on 31 Mar. (2001)) wherein ammonium formate/palladium-on-charcoal or H$_2$/palladium-on-charcoal assisted reduction of crude calamus oil containing high percentage of toxic β-asarone provides 2,4,5-trimethoxyphenylpropane (dihydro asarone) of the formula I in 97% purity with yield ranging from 81–87% based on asarones content in calamus oil. Thus, obtained 2,4,5-trimethoxyphenylpropane (or 1-Propyl-2,4,5-trimethoxykenzene) is tested for the first time as five times less toxic than β-asarone and thus, this 2,4,5-trimethoxyphenylpropane enables its application in the products such as mouth washes, tooth pastes, antiseptic soap products, chewing gum flavors and little in spicy products due to its sweet, ylang, slightly spicy and fruity aroma. In addition, 2,4,5-trimethoxyphenylpropane is also discovered as a simple and an economical starting material for synthesis of a salicylamide based antipsychotic drug (5,6-dimethoxy-N[(1-ethyl-2-pyrrolidinyl)methyl]-3-propylsalicylamide) (Thomas, H.; Stefan, B.; Tomas, D. P.; Lars, J.; Peter, S.; Hakan, H. and Orgen, S. J. O., Med. Chem., 33, 1155–1163 (1990) and Sinha, A. K., U.S. patent application Ser. No. 09-652376 filed on 31 Aug. (2000)). In the present invention, we have extended the scope of further exploiration of 2,4,5-trimethoxyphenylpropane of the formula I as simple and economical starting material towards the formation of novel neolignan (3-ethyl-2-methyl-3-(2", 4",5"-trimethoxy)phenyl-1-(2',4',5'-trimethoxy)phenyl-1-propene) (named as NEOLASA-I) of the formula II and its dihydro derivative (3-ethyl-2-methyl-3-(2",4",5"-trimethoxy)phenyl-1-(2',4',5'-trimethoxy)phenylpropane) (named as NEOLASA-II of the formula III and side products α-asarone of the formula II and 1-2,4,5-trimethoxy) phenyl-1-propanone (isoacoramone) of the formula IIb thereof which are, in fact, biologically active rarer phenylpropanoids.

Keeping in view, the toxicity problem of widely available β-asarone rich *Acorus calamus* oil, our initial attempt was to utilize β-asarone as a simple and cheaper starting material for the synthesis of pharmacologically active α-asarone via dihydro product of β-asarone i.e. 2,4,5-trimethoxyphenylpropane. With this objective, 2,4,5-trimethoxyphenylpropane was treated with mercuric acetate or DDQ in acetic acid to provide intermediate 1-(2,4,5-trimethoxy)phenyl-1-acetoxypropane followed by alkaline hydrolysis and acidic dehydration towards formation of α-asarone (Wang, Z.; Jiang, L. and Xingxiang, X., Youji Huaxue, 10 (4), 350–352 (1990); Shirokova, E. A.; Segal, G. M. and Torgov, I. V., Bioorg. Khim., 11 (2), 270–275 (1985) and Janusz, P.; Bozena, L.; Alina, T. D.; Barbara, L.; Stanislaw, W.; Danuta, S.; Jacek, P.; Roman, K.; Jacek, C.; Malgorzata, S. and Zdzislaw, C., J. Med. Chem., 43, 3671–3676 (2000)). Treatment of benzylic compounds such as 8,9,10,11-tetrahydrodibenz(a,h)acridine and stegane with mercuric acetate/acetic acid or DDQ/acetic acid is well documented in literature towards formation of corresponding acetate (Subodh, K., J. Org. Chem., 50, 3070–3073 (1985) and Ward, R. S., Tetrahedron Letters, 48 (15), 5029–5041 (1990)). However, 2,4,5-trimethoxyphenylpropane (benzylicalkane) failed to produce any kind of product with mercuric acetate/acetic acid under the above analogue reaction condition. Interestingly, 2,4,5-trimethoxyphenylpropane/DDQ/AcOH also failed to produce expected 1-(2,4,5-trimethoxy)phenyl-1-acetoxypropane, but, it provided a mixture of interesting products which were easily purified on column chromatography and identified as α-asarone of the formula IIa, 1-(2,4,5-trimethoxyphenyl)-1-propanone (isoacoramone) of the formula IIb and novel neolignan of the formula II as a crystalline solid having three different mp 44–45° C., 109–110° C. and 96–97° C. respectively. The structure of (α-asarone (mp 44–45° C.) was assigned and identified on the basis of spectral data (Example II). Similarly, structure of crystalline solid having mp 109–110° C. was confirmed on the basis of spectral data in which IR absorption band appeared at 1658 (conjugated C=O) cm$^{-1}$ and also gave a positive 2,4-DNP test, thus, confirming the presence of carbonyl group. $^1$H NMR showed the 16 number of protons (Example II) which is less by two number of protons in comparison to starting material 2,4,5-trimethoxyphenylpropane (Example I) except for a triplet signal at δ 1.18 (3H, t, J=6.9 Hz) and quartet signal at 2.99 (2H, q, J=6.9 Hz) which could be assigned to a methylene proton coupled with a methyl group proton which is overall indicative of ethyl group. Further, the position of two aromatic singlet protons and three singlet for nine protons from trimethoxy groups are more or less at same 67 value as starting material, however, appearance of ethyl protons at δ 1.18 (2H, t), 2.99 (3H, q) and carbonyl group (1658 cm$^{-1}$) finally supported the possibility of ethylketone (—CO—CH$_2$—CH$_3$) attached to trimethoxy substituted phenyl ring. Similarly, the $^{13}$C NMR and DEPT spectral data further supported the presence of ethyl group (δ$_c$ 8.4 CH$_3$; δ$_c$ 36.9 CH$_2$) and the ketonic carbonyl (δ$_c$ 200.5) linked directly to the benzene ring (Example III). The EI mass spectrum showed a clear [M]$^+$ peak at m/z 224 along with base peak at m/z 195 (M$^+$−29) which was in agreement with the presence of an ethyl moiety and this together with above $^1$H, $^{13}$C and IR data, the crystalline solid (mp 109–110° C.) was finally confirmed to, be 1-(2,4,5-trimethoxyphenyl)-1-propanone (also known as isoacoramone) which is later on discovered as a naturally occurring rarer phenylpropanoid., isolated from *Piper marginatum* and *Acorus tatarinowii* as a light yellowish viscous gum in traces, however, our method afforded isoacoramone as a crystalline solid (mp 109–110° C.) (Example II) with the similar spectral data as natural isoacoramone (Jinfeng, Hu and Xiaozhang, Feng, Planta Medica, 66, 662–664 (2000)). Thus, preparation of 2,4,5-trimethoxypropiophenone (isoacoramone) in sufficient quantity has allowed to facilitate its more rigorous biological evaluation known for structurally similar propiophenone derivatives (Kuchar, M.; Brunova, B.; Rejholec, V.; Roubal, Z. and Nemecek, O., Collection Czechoslov. Chem., 41, 633–646 (1976); Lariucci, C.; Homar, L. I. B.; Ferri, P. H. and Santos, L. S., Anais Assoc. Bras. Quim., 44(3), 22–27 (1995); Stauffer, S. R.; Coletta, C. J.; Tedesco, R.; Nishiguchi, G.; Carlson, K.; Sun, J.; Katzenellenbogen, B. S. and Katzenellenbogen, J. A., J. Med. Chem., 43, 4934–4947 (2000) and Jaimol, T.; Moreau, P.; Finiels, A.; Ramaswamy, A. V. and Singh, A. P., Applied Catalysis A: General, 214, 1–10 (2001). Additionally, 2,4,5-trimethoxypropiophenone (isoacoramone) can be utilized as a simple synthon for the preparation of diarylbutane type lignan as an analogue of nordihydroguaiaretic acid (NDGA acid) which is prepared by dimerization of 4,5-dimethoxypropiophenone (Perry, C. W. U.S. Pat. No. 3,769, 350 (1975)).

In order to establish the structure of third crystalline solid having mp 96–97° C., a comprehensive investigation of NMR spectral data recorded in two solvents (CDCl$_3$ and DMSO-d$_6$) for better clarity and separation of each peaks was undertaken. The electrospray (ES)-mass spectrum of crystalline solid gave molecular ion at m/e 418 (M$^+$). The $^1$H NMR spectra of solid (mp 96–97° C.) showed the presence of six methoxyls indicating it to be a possible dimer of asarone like phenylindane (a unsymmetrical dimer reported from *Acorus calamus*) (Saxena, D. B. Phytochemistry 25 (2), 553–555 (1986)) but with change in side chain structure. It is interesting to note from the aromatic region integrated for the four protons indicating that none of aromatic proton participates in dimerisation, however, one of the aromatic proton of phenylindane (2,3-dihydro-4,5,7-trimethoxy-1-ethyl-2-methyl-3-(2,4,5-trimethoxyphenyl)indene) has taken part in dimerisation. The other groups found to be an ethyl group appeared at δ 0.93 (3H, t, H-5), 1.70–1.97 (2H, m, H-4), 3.59 (1H, t, H-3), a tertiary methyl group 1.66 (3H, s, H-6) and a alkene proton on a carbon atom attached to the phenyl ring 6.48 (1H, s, H-1). The above skeleton is further supported by $^{13}$C (DEPT-135°) spectra data and mass fragmentation pattern m/z: 418 (M$^+$) (Example II). On the basis of above spectral data and further, its comparison with some known neolignans such as Magnoshinin, Magnosalin and Heterotropan (Kikuchi, T.; Kadota, S.; Yanada, K.; Tanaka, K.; Watanabe, K.; Yoshozaki, M.; Yokoi, T. and Shingu, T., Chem. Pharm. Bull. 31, 1112 (1983); Yamamura, S.; Niwa, M.; Nonoyama, M. and Terada, Y. Tetrahedron Letters, 4891 (1978) and Kadota, S.; Tsubono, K.; Makino, K.; Takeshita, M. and Kikuchi, T., Tetrahedron Letters, 28 (25), 2857–2860 (1987)) having some degree of similarity in their structure (Wenkert, E.; Gottlieb, H. E.; Gottlieb, O. R.; Pereira, M. O. D. S. and Formiga, M. D., Phytochemistry, 15, 1547–1551 (1976), the crystalline solid is identified as neolignan i.e. 3-ethyl-2-methyl-3-(2″,4″,5″-trimethoxy)phenyl-1-(2′,4′,5′-trimethoxy) phenyl-1-propene) (named as NEOLASA-I) (Example II). Further, neolignan (NEOLASA-I) is hydrogenated (Example III) to obtain its corresponding dihydro product i.e. 3-ethyl-2-methyl-3-(2″,4″,5″-trimethoxy) phenyl-1-(2′,4′,5′-trimethoxy)phenylpropane (named as NEOLASA-II so as to confirm the structure as well as to determine the position of double bond existing in the above parent neolignan (NEOLASA-I) which may additionally serve as a simple synthon towards preparation of neolignans derivatives in sufficient quantity to have opportunity for a wide range of biological activities including antifungal, antioxidant, anti-inflammatory, neuroleptic, anti-hepatotoxic, anticancer, anti-HIV and anti-PAF activities known for structurally similar neolignan derivatives. Neolignans and lignans comprise a class of natural plant products and they are found in the roots, stems, bark, fruit and seeds of many plant species. More than 200 compounds in this general class have been identified and a great diversity in the chemical assembly of the two characteristic phenylpropanoid units, as well as degree of oxidation and types of substituents is apparent. In addition, some natural lignans/neolignans are used as starting materials for the semi-synthesis of biological active compounds such as podophyllotoxin, isolated from *Podophyllum* species, is used for the semi-synthesis of the anticancer compounds etoposide and teniposide (Stähelin, H. F. and Wartburg, A. V., Cancer Research, 51, 5–15 (1991)). A number of chemical reviews on natural as well as synthetic neolignans and lignans are available including their biological activities. However, neolignas/lignans are found in traces in plant kingdom and for these reasons, several methods of preparation of neolignas/lignans have been developed by several chemists and some of the reported conventional methods include the following.

Typical prior art refrences include Iguchi, M., Nishiyama, A., Terada, Y. and Yamamura, S., Tetrahedron, 51, 4511–4514 (1977); McKillop, A.; Turrell, A. G. and Taylor, E. C., J. Org. Chem., 765 (1977); Minato, A.; Tamao, K.; Suzuki, K. and Kumada, M., Tetrahedron Letters, 21, 40174020 (1980); Cambie, R. C.; Clark, G. R.; Craw, P. A.; Rutledge, P. S. and Woodgate, P. D., Aust. J. Chem., 1775 (1984); Kadota, S., Tsubono, K., Makino, K., Takeshita, M and Kikuchi, T., Tetrahedron Letters, 28 (25), 2857–2860 (1987); Dhal, R.; Landais, Y.; Lebrun, A.; Lenain, V. and Robin, J. P., Tetrahedron, 50(4), 1153–1164 (1994); Meyers, M. J.; Sun, J.; Carlson, K. E.; Marriner, G. A.; Katzenellenbogen, B. S. and Katzenellenbogen, J. A., J. Med. Chem., 44, 4230–4251 (2001): Gezginci, M. H. and Timmermann, B. N., Tetrahedron Letters, 42, 6083–6085 (2001); Robin, J. P. and Yannick, L., Tetrahedron, 48 (5), 819–830 (1992) and U.S. Pat. Nos. 3,769,350; 4,873,349 and 6,136,992.

All the above methods including patents have various limitations and none of them have been found suitable for the economical production of neolignan derivative. In seeking a simple synthesis of neolignan derivatives from a cheaper material and reagents, 2,4,5-trimethoxyphenylpropane (isolated from hydrogenation of commercially available *Acorus calamus* oil rich in asarones content) appears as a simple and economical starting material in which 2,4,5-trimethoxyphenylpropane undergoes dehydrogenation, oxidation and demerisation to afford 3-ethyl-2-methyl-3-(2",4",5"-trimethoxy)phenyl-1-(2',4',5'-trimethoxy)phenyl-1-propene (NEOLASA-I) as well as rarer phenylpropanoids namely α-asarone and isoacoramone. In the present invention, the formation of neolignan (NEOLASA-I) and its dihydro product (NEOLASA-II) are the first example of DDQ assisted one step synthesis of dimer from phenylpropane derivatives which, in fact, would offer the advantages of simplicity and directness and can be applied for large scale preparations.

EXAMPLES

The invention will now be described by way of example with refrence to the accompanying examples, which are provided for the purpose of illustration and are not to be constructed as being limiting on the present invention.

Example 1
Preparation 2,4,5-trimethoxyphenylpropane (dihydro asarone): The starting material 2,4,5-trimethoxyphenylpropane is prepared by hydrogenation of either β-asarone (isolated from *Acorus calamus* oil) or commercially available calamus oil rich in asarones (i.e. β and/or α,γ-asarone) content.
(a) Hydrogenation of β-asarone into 2,4,5-trimethoxyphenylpropane (dihydro asarone): β-asarone was isolated by loading the crude calamus oil (17.00 g) on silica gel column and then eluted the column with hexane to remove unwanted non-polar compounds. Subsequent elution with hexane-ethylacetate mixture with increasing proportion of ethylacetate up to 10% gave 13.94 g (82%, w/w) of pure liquid; $R_f$ 0.63 (hexane:toluene: ethylacetate= 1:1:0.1); $^1$H NMR (CDCl$_3$, 300 MHz) δ 6.84 (1H, s, H-6), 6.53 (1H, s, H-3), 6.50 (1H, dd, J=15.8 Hz and 1.5 Hz, H-1'), 5.78 (1H, dq, J=6.5 Hz and 15.8 Hz, H-2'), 3.88, 3.83 and 3.79 (s, 3H, each, 3-OCH$_3$) and 1.85 (3H, dd, J=6.5 Hz and 1.5 Hz, H-3$^1$); $^{13}$C NMR (CDCl$_3$, 75.4 MHz) δ 151.4 (C-2), 148.5 (C-4), 142.3 (C-5), 125.5 (C-1'), 124.7 (C-2'), 118.0 (C-1), 114.1 (C-6), 97.6 (C-3), 56.5, 56.2 & 55.9 (3×OCH$_3$) and 14.5 (C-3'); EIMS m/z 208 (M$^+$, 100), 193 (M$^+$-Me, 46), 165 (M$^+$-C$_3$H$_7$, 24). On the basis of above spectral data and comparing with reported literature (Gonzalez, M. C.; Sentandrew, M. A.; Rao, K. S.; Zafra, M. C. and Cortes, D., Phytochemistry 43,1361–1364 (1996)), the liquid was identified as β-asarone in 94% purity (by GC, performed on a Shimadzu-GC-14B gas chromatograph with the following conditions: SE-30 column; 30 m×0.25 mm; injector 250°/C; FID detector 230°/c; temp. programme 40 (hold for 2 min.) to 220° C. (hold for 10 min.), 10° c. min$^{-1}$; vol. 1 μl; N$_2$ flow 30 ml/min; H$_2$ flow 40 ml/min.; airflow 300 ml/min.; split injection ratio 1:30)

The β-asarone (6.00 g, 0.029 mol) in 160 ml of ethanol is stirred with 10% palladium on activated charcoal (0.80 g) and ammonium formate (17.00 g, 0.27 mol) at room temperature under nitrogen atmosphere until the disappearance of starting material. The catalyst was removed by filtration and the solvent was evaporated under reduced pressure. The residue was partitioned between ethyl acetate and water and the ethyl acetate layer washed with water, dried (Na$_2$SO$_4$) and filtered. Evaporation of filtrate left a liquid, which was chromatographed, on silica gel using hexane-ethyl acetate mixture with increasing proportion of ethyl acetate up to 10% as the eluent. The eluate was evaporated to give 5.87 g (97%) of a clear sweet and pleasant liquid; $R_f$ 0.69 on silica gel plate (hexane:toluene:ethylacetate=1:1:0.1) which solidified below 0° C.;
$^1$H NMR (DMSO-d6) δ 6.72 (1H, s, H-6), 6.62 (1H, s, H-3), 3.76 to 3.68 (9H, s, 3-OCH$_3$), 2.5 (2H, t, C-1'), 1.6 (2H, m, C-2') and 0.9 (3H, t, C-3'); $^{13}$C NMR (CDCl$_3$) δ 151.4 (C-2), 147.4 (C-4), 142.7 (C-5), 122.7 (C-1), 114.3 (C-6), 98.0 (C-3) and 56.5, 56.2 & 56.0 (3× OCH$_3$), 31.6 (C-1'), 23.3 (C-2') and 13.79 (C-3'); EIMS m/z 210 (M$^+$, 39), 181(M$^+$-C$_2$H$_5$ 100), 167 (M$^+$-C$_3$H$_7$, 151 (M$^+$-OCH$_3$+CO, 29), 136 (M$^+$-C$_3$H$_7$+OCH$_3$, 10). On the basis of $^1$H NMR, $^{13}$C NMR and Mass spectral data, the above liquid was identified as 2,4,5-trimethoxyphenylpropane in 99% purity (by GC).
(b) Hydrogenation of crude *Acorus calamus* oil into dihydro asarone: In this method 42.00 g of crude calamus oil (rich in β and/or α,γ-asarone) in 300 ml methanol was hydrogenated in the parr reactor with 10% Pd/C (4.80 g) at 10–40 psi at room temperature till the disappearance of starting material. The catalyst was filtered and the solvent was removed under reduced pressure, which afforded 39.9 g (95 w/w) of reduced oil. Column purification of reduced oil on silica gel column using above eluent system (hexane-ethyl acetate mixture) gave 2,4,5-trimethoxyphenylpropane (35.76 g) as a liquid in 85% yield (w/w); $R_f$ 0.69 (hexane:toluene:ethylacetate= 1:1:0.1); $^1$H NMR (CDCl$_3$) of liquid appeared at δ 6.81 (1H, s, H-6), 6.32 (1H, s, H-3), 3.84 to 3.78 (9H, s, 3-OCH$_3$), 2.4 (2H, t, C-1'), 1.6 (2H, m, C-2'), 0.9 (3H, t, C-3'). On the basis of spectral data, the liquid was identified as 2,4,5-trimethoxyphenylpropane.

Example II

Preparation of 3-ethyl-2-methyl-3-(2",4",5"-trimethoxy) phenyl-1-(2',4',5'-trimethoxy)phenyl-1-propene: DDQ (6.13–7.97 g) was added over a period of 10–15 min to a ice cold and well stirred solution of 2,4,5-trimethoxyphenylpropane (5.67 g, 0.027 mol) in acetic acid (55 mL) and stirring was continued at room temperature for over night. The precipitated solid of DDQH$_2$ was filtered and the filter cake washed twice with acetic acid. In addition to acetic acid, other organic acids, such as propionic acid, may be used. The combined acetic acid layer was evaporated and mixture was poured into water and extracted with dichloromethane (3×70 mL). In addition to dichloromethane, other aliphatic halogenated hydrocarbons, such as carbontetracholride or chloroform, may be used. The combined organic layer were washed with brine (3×15 mL), 10% sodium bicarbonate (2×10 mL), brine (3×15 mL) and dried over sodium sulphate. The residue obtained on evaporation of the solvents was chromatographed on silica gel using hexane-ethyl acetate mixture with increasing proportion of ethyl acetate up to 40% and the fractions having similar $R_f$ were mixed which after evaporation of solvents provided three viscous liquids which were further crystallized from mixture of hexane and methanol to afford three white solids having mp 44–45° C., 109–110° C. and 96–97° C. with 9%, 22% and 32% yield respectively.

White solid having mp 44–45° C. was identified as α-asarone (9%); $R_f$ 0.63 (hexane:toluene:ethylacetate: 1:1:0.1); $^1$H NMR (CDCl$_3$): δ 6.91 (1H, s, H-6), 6.64 (1H, dd, J=1.5 Hz and 16 Hz, H-1'), 6.45 (1H, s, H-3), 6.02 (1H, dq, J=6.2 Hz and 16.0 Hz, H-2'), 3.84, 3.81 and 3.77 (each 3H, s, three OCH$_3$), 1.87 (3H, dd, J=6.2 Hz and 1.5 Hz, H-3$^1$); $^{13}$H NMR (CDCl$_3$): δ 149.9 (C-2), 148.0 (C-4), 142.6 (C-5), 124.4 (C-1'), 123.4 (C-2'), 118.3 (C-1), 109.2 (C-6), 97.3 (C-3), 56.1, 55.7 & 55.1 (3-OCH$_3$), 18.7 (C-3'); EIMS m/z 208 (M$^+$100), 193 (74), 177 (24), 165 (26), 137 (12), 105 (8), 91 (26), 77 (24), 69 (34), 65 (8), 53 (16). On the basis of above spectral data and comparing with reported-literature (Patra, A. and Mitra, A. K., J. Nat. Prod. 44, 668–669 (1981) and Gonzalez, M. C.; Sentandrew, M. A.; Rao, K. S.; Zafra, M. C. and Cortes, D., Phytochemistry 43:1361–1364 (1996)), the structure of white solid (mp 44–45° C.) was finally confirmed as α-asarone.

Another white solid (22%) having mp 109–110° C. was identified as 1-(2,4,5-trimethoxy)phenyl-1-propanone; $R_f$ 0.78 (28% ethylacetate in hexane); $^1$H NMR (CDCl$_3$) at δ 7.45 (1H, s, H-6), 6.77 (1H, s, H-3), 3.96, 3.93 and 3.89 (each 3H, s, three OCH$_3$), 2.99 (2H, q, J=6.9 Hz, H-2'), 1.18 (3H, J=6.9 Hz, H-3'); $^{13}$C NMR (CDCl$_3$, 75.4 MHz) δ 200.5 (C-1'), 155.0 (C-2), 153.4 (C-4), 142.8 (C-5), 118.9 (C-1), 112.6 (C-6), 96.3 (C-3), 56.1 (4-OCH$_3$ and 5-OCH$_3$), 55.9 (2-OCH$_3$), 36.9 (C-2'), 8.4 (C-3'); EIMS m/z 224 [M]$^+$ (16), 195 (100), 179 (14), 171 (10), 151 (7), 69 (15); IR (KBr) 1658 cm-1 (C=O). On the basis of above spectral data and comparing with reported literature ((Jinfeng, Hu and Xiaozhang, Feng, Planta Medica, 66, 662–664 (2000)), the structure of another white solid (mp 109–110° C.) was confirmed as 1-(2,4,5-trimethoxy)phenyl-1-propanone (or isoacoramone).

Third white solid (32%) having mp 96–97° C. was identified as (3-ethyl-2-methyl-3 -(2",4",5"-trimethoxy)phenyl-1-(2',4',5'-trimethoxy)phenyl-1-propene); $R_f$ 0.45 (20% ethylacetate in hexane); $^1$H NMR (CDCl$_3$) δ 6.91 (1H, s, H-6'), 6.84 (1H, s, H-6"), 6.55 (1H, s, H-3'), 6.51(1H, s, H-3"), 6.48 (1H, s, H-1), 3.96 (6H, s, 2'-OCH$_3$ and 2"-OCH$_3$), 3.84 (6H, s, 4'-OCH$_3$ and 4"-OCH$_3$), 3.80 (3H, s, 5'-OCH$_3$), 3.78 (3H, s, 5"-OCH$_3$), 3.59 (1H, t, H-3), 1.70–1.97 (2H, m, H-4), 1.66 (3H, s, H-6), 0.9 $^1$H NMR ((DMSO-d$_6$) δ 6.79 (1H, s, H-6'), 6.68 (1H, s, H-6"), 6.67 (1H, s, H-3'), 6.66(1H, s, H-3"), 6.34 (1H, s, H-1), 3.84 (9H, s, 2"-OCH$_3$, 4"-OCH$_3$ and 5"-OCH$_3$), 3.68(3H, s, 2'-OCH$_3$), 3.66(3H, s, 4'-OCH$_3$), 3.62 (3H, s, 5'-OCH$_3$), 3.53 (1H, t, H-3), 1.88–1.67 (2H, m, H-4), 1.60 (3H, s, H-6), 0.84 (3H, t, H-5); $^{13}$C NMR (CDCl$_3$), 3.53 (1H, t, H-3), (C-2'), 152.02 (C-2"), 148.48 (C-4'), 147.94 (C-4"), 143.57 (C-5'), 142.89 (C-5"), 140.41 (C-2), 124.88 (C-1'), 120.18 (C-1), 119.65 (C-1"), 114.88 (C-6'), 112.14 (C-6"), 99.47 (C-3'), 99.33 (C-3"), 57.37 (5"-OCH$_3$), 57.09 (5'-OCH$_3$), 57.07 (4"-OCH$_3$), 56.94 (4'-OCH$_3$), 56.55 (2"-OCH$_3$), 56.48 (2'-OCH$_3$), 47.38 (C-3), 26.74 (C-4), 17.82 (C-6), 12.84 (C-5); $^{13}$C NMR (DMSO-d$_6$) δ 152.56 (C-2'), 152.11 (C-2"), 149.07 (C-4'), 148.53 (C-4"), 143.53 (C-5'), 142.84 (C-5"), 139.45 (C-2), 123.96 (C-1'), 120.56 (C-1), 119.09 (C-1"), 115.47 (C-6'), 113.02 (C-6"), 99.55 (C-3'), 99.23 (C-3"), 57.39 (5"-OCH$_3$), 57.24 (5'-OCH$_3$), 57.17 (4"-OCH$_3$), 57.08 (4'-OCH$_3$), 56.63 (2"-OCH$_3$), 56.59 (2'-OCH$_3$), 47.56 (C-3), 26.46 (C-4), 17.71 (C-6), 13.33 (C-5); NMR (DEPT-135°) δ 120.56 (C-1), 115.47 (C-6'), 113.02 (C-6"), 99.55 (C-3'), 99.23 (C-3"), 57.39 (5"-OCH$_3$), 57.24 (5'-OCH$_3$), 57.17 (4"-OCH$_3$), 57.08 (4'-OCH$_3$), 56.63 (2"-OCH$_3$), 56.59 (2'-OCH$_3$), 47.56 (C-3, down), 26.46 (C-4), 17.71 (C-6), 13.33 (C-5); EIMS m/z 416 [M]$^+$ (14), 219 (100), 209 (47), 181(21), 171 (20), 71 (27).

Addition of a large excess of DDQ (8.58–12.87 g) in above said process using 5.67 g, of 2,4,5-trimethoxyphenylpropane in acetic acid (55 mL), improved the yield of 1-(2,4,5-trimethoxy)phenyl-1-propanone up to 39%, however, reduction in the yield of 3-ethyl-2-methyl-3-(2",4",5"-trimethoxy)phenyl-1-(2',4',5'-trimethoxy)phenyl-1-propene (16%) α-asarone (10%) was observed.

Example III

Preparation of 3-ethyl-2-methyl-3-(2",4",5"-trimethoxy)phenyl-1-(2',4',5'-trimethoxy)phenylpropane: 0.20 mg of 5% Pd/C was added to a solution of 3-ethyl-2-methyl-3-(2", 4",5"-trimethoxy)phenyl-1-(2',4',5'-trimethoxy)phenyl-1-propene (0.35 g, 0.84 mmole) in ethyl acetate (40 mL) and methanol (25 mL) and was shaken under atmosphere of hydrogen in paar reactor (5–20 psi) at room temperature till the disappearance of starting material. The catalyst was filtered and the solvent was removed under reduced pressure, which afforded a liquid. The liquid was purified on silica gel using above eluent system (hexane-ethyl acetate mixture) gave 3-ethyl-2-methyl-3-(2",4",5"-trimethoxy)phenyl-1-(2',4',5'-trimethoxy)phenylpropane (0.32 g) as a liquid in 91% yield; $R_f$ 0.47 (20% ethylacetate in hexane); $^1$H NMR (CDCl$_3$) δ 6.77 (1H, s, H-3"), 6.68 (1H, d, H-6"), 6.54 (1H, d, H-6'), 6.51(1H, s, H-3'), 3.96 (6H, s, 2'-OCH$_3$ and 2"-OCH$_3$), 3.84 (6H, s, 4'-OCH$_3$ and 4"-OCH$_3$), 3.80 (3H, s, 5"-OCH$_3$), 3.78 (3H, s, 5"-OCH$_3$), 2.60 (2H, d, H-1), 2.08 (1H, t, H-3), 1.95 (1H, m, H-2), 1.92–1.57(2 H, m, H-4), 0.88(3H, d, H-6), 0.82(3H, t, H-5); EIMS m/z 418 [M]$^+$ (14), 209 (100), 179 (14), 181 (29), 151 (9), 69 (6).

The main advantages of the present invention are:
1. The process to prepare 3-ethyl-2-methyl-3-(2",4",5"-trimethoxy)phenyl-1-(2',4',5'-trimethoxy)phenyl-1-propene, a novel neolignan, along with side products in single step from 2,4,5-trimethoxyphenylpropane using DDQ as a mild and efficient reagent for the first time.
2. The process for the commercial utilization of internationally banned but widely available toxic β-asarone from *Acorus calamus* oil of tetraploid or hexaploid varieties (distributed extensively in Asian countries), thereby, enhancing the profitable use thereof.
3. The simple process which discloses the formation of new kind of products by the interaction of 2,4,5-trimethoxyphenylpropane with varying amount of DDQ and time, temperature and solvents.
4. The simple process which involves the conversion of mixture of all the three isomeric forms of phenylpropene i.e. α,β and γ-asarone firstly into 2,4,5-trimethoxyphenylpropane and then utilizing it as a simple synthon for the preparation of 3-ethyl-2-methyl-1-(2',4', 5'-trimethoxy)-phenyl)-3-(2",4",5"-trimethoxy)phenyl-1-propene and side products α-asarone and 1-(2,4,5-trimethoxy)phenyl-1-propanone thereof.
5. The process provides neolignan and side products α-asarone and 1-(2,4,5-trimethoxy)phenyl-1-propanone in high purity.

6. The process provides 2,4,5-trimethoxypropiophenone as a solid compound whereas, natural 2,4,5-trimethoxypropiophenone (isolated from *Acorus tatarinowii* and *Piper marginatum*) is reported as viscous gum.
7. The process provides 1-(2,4,5-trimethoxy)phenyl-1-propanone in sufficient quantity and thus provides the opportunity for the evaluation of its wide range of biological activities known for structurally similar phenylpropanone derivatives.
8. The process provides novel neolignan in sufficient quantity and thus provides the opportunity for the evaluation of its wide range of biological activities known for structurally similar neolignans.
9. The process provides novel neolignan as a crystalline solid with m.p. ranging from 96°–97C.
10. The process provides novel neolignan (NEOLASA-I) having one asymmetric center and one double bond in aliphatic side chain which is further capable of undergoing conversion into several naturally occurring neolignan and lignan derivatives.
11. The process provides novel dihydro neolignan i.e. 3-ethyl-2-methyl-3-(2",4",5"-trimethoxy)phenyl-1-(2',4',5'-trimethoxy)phenylpropane (NEOLASA-11) by hydrogenation of 3-ethyl-2-methyl-3-(2",4",5"-trimethoxy) phenyl-1-(2',4',5'-trimethoxy)phenyl-1-propene (NEOLASA-II).
12. The process provides a novel dihydro neolignan in sufficient quantity via simple and economical route, thus, providing an opportunity for its biological evaluation.
13. The process provides a novel dihydro (NEOLASA II) which is capable of undergoing conversion into several naturally occurring neolignan and lignan derivatives.

What is claimed is:

1. A process for the preparation of neolignan 3-ethyl-2-methyl-3-(2",4",5"-trirnethoxy) phenyl-1-(2',4',5'-trimethoxy) phenyl-1-propene from toxic β-asarone or β-asarone rich *Acorus calamus* oil containing α and γ-asarone, the said process comprising the following steps:

a) hydrogenating β-asarone or β-asarone rich *calamus* oil containing α and γ-asarone in presence of methanol or ethanol, 10% Pd/C catalyst, with or without ammonium formate under pressure between 0–40 psi at room temperature,
b) purifying the product of step (a) over silica gel column to obtain 2,4,5-trimethoxyphenylpropane of formula (I),

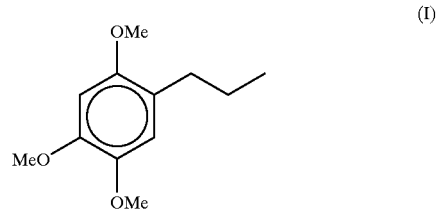

c) stirring the compound of formula (I) of step (b) with DDQ in presence of organic solvent selected from group of acetic acid or propionic acid at room temperature for overnight,
d) filtering the precipitate solid of $DDQH_2$ and washing the filtrate twice with acetic acid,
e) evaporating the filtrate of step (d), to obtain a concentrated mixture,
f) extracting the mixture of (e) with dichloromethane wherein the mixture of acetic acid and dichloromethane forms an organic layer,
g) washing the organic layer of step (f) with brine followed by 10% sodium bicarbonate and another second washing with brine,
h) drying the organic layer obtained in step (g) over anhydrous sodium sulphate, wherein a residue is formed,
i) chromatographing the residue of step (h) over silica gel using hexane-ethyl acetate mixture to obtain three sets of fractions, and
j) crystallizing fractions of step (i) using mixture of hexane and methanol, and
k) obtaining crystallized fractions of 2,4,5-trimethoxyphenylpropane of formula I, 1-(2,4,5-trimethoxy) phenyl-1-propanone and 2,4, neolignan 3-ethyl-2-methyl-3-(2",4",5"-trimethoxy) phenyl-1-(2', 4',5'-trimethoxy)phenyl-1-propene.

2. A process as claimed in claim 1 wherein the effective molar ratio of 2,4,5-trimethoxy propane and DDQ in step (c) is in the range of 1:1 to 1:2.1.

3. A process as claimed in claim 1, wherein the organic solvent in step (c) is acetic acid.

4. A process as claimed in claim 1 wherein the neolignan obtained is termed as NEOLASA-I.

5. A process as claimed in claim 1, wherein the said neolignan has one asymmetric center.

6. A process as claimed in claim 1, wherein the said neolignan obtained provides the opportunity for evaluation of its biological activity.

7. A process as claimed in claim 1, wherein the said neolignan has aliphatic side chain with one double bond.

* * * * *